(12) United States Patent
Ichikawa

(10) Patent No.: US 11,510,647 B2
(45) Date of Patent: Nov. 29, 2022

(54) BACKING MEMBER AND ULTRASONIC PROBE INCLUDING LEADS AND SPACERS EMBEDDED IN A RESIN BODY

(71) Applicant: SHINKO ELECTRIC INDUSTRIES CO., LTD., Nagano (JP)

(72) Inventor: Sumihiro Ichikawa, Nagano (JP)

(73) Assignee: SHINKO ELECTRIC INDUSTRIES CO., LTD., Nagano (JP)

(*) Notice: Subject to any disclaimer, the term of this patent is extended or adjusted under 35 U.S.C. 154(b) by 498 days.

(21) Appl. No.: 16/257,169

(22) Filed: Jan. 25, 2019

(65) Prior Publication Data
US 2019/0231308 A1 Aug. 1, 2019

(30) Foreign Application Priority Data
Jan. 26, 2018 (JP) .............................. JP2018-011897

(51) Int. Cl.
| | | |
|---|---|---|
| A61B 8/00 | (2006.01) | |
| G10K 11/00 | (2006.01) | |
| H01L 41/08 | (2006.01) | |
| G10K 11/16 | (2006.01) | |
| H01L 41/04 | (2006.01) | |
| H04R 17/00 | (2006.01) | |

(52) U.S. Cl.
CPC .......... *A61B 8/4444* (2013.01); *A61B 8/4272* (2013.01); *A61B 8/4483* (2013.01); *G10K 11/002* (2013.01); *G10K 11/16* (2013.01); *H01L 41/04* (2013.01); *H01L 41/08* (2013.01); *H04R 17/00* (2013.01)

(58) Field of Classification Search
CPC ... A61B 8/4444; A61B 8/4272; A61B 8/4483; G10K 11/002; G10K 11/16; H01L 41/04; H01L 41/08; H04R 17/00
USPC ......................................................... 310/227
See application file for complete search history.

(56) References Cited

U.S. PATENT DOCUMENTS

| | | | |
|---|---|---|---|
| 5,592,730 A | 1/1997 | Greenstein et al. | |
| 2011/0108838 A1* | 5/2011 | Kageyama | H04R 19/016 257/416 |
| 2017/0338398 A1* | 11/2017 | Sorimachi | H01L 41/0475 |

FOREIGN PATENT DOCUMENTS

| | | |
|---|---|---|
| JP | H08-065797 A | 3/1996 |
| JP | 2015-228932 | 12/2015 |

OTHER PUBLICATIONS

Japanese Office Action with English Translation dated Oct. 5, 2021, 8 pages.

* cited by examiner

Primary Examiner — Emily P Pham
Assistant Examiner — Monica Mata
(74) Attorney, Agent, or Firm — Rankin, Hill & Clark LLP

(57) ABSTRACT

A backing member includes: a resin body including a lower surface and an upper surface opposite to each other; a plurality of leads each of which extends in a first direction from the lower surface toward the upper surface, and that are embedded at pitches in the resin body; and a plurality of insulating spacers each of which is provided between adjacent ones of the leads and extends in a second direction intersecting with the first direction, and that contact the leads.

8 Claims, 32 Drawing Sheets

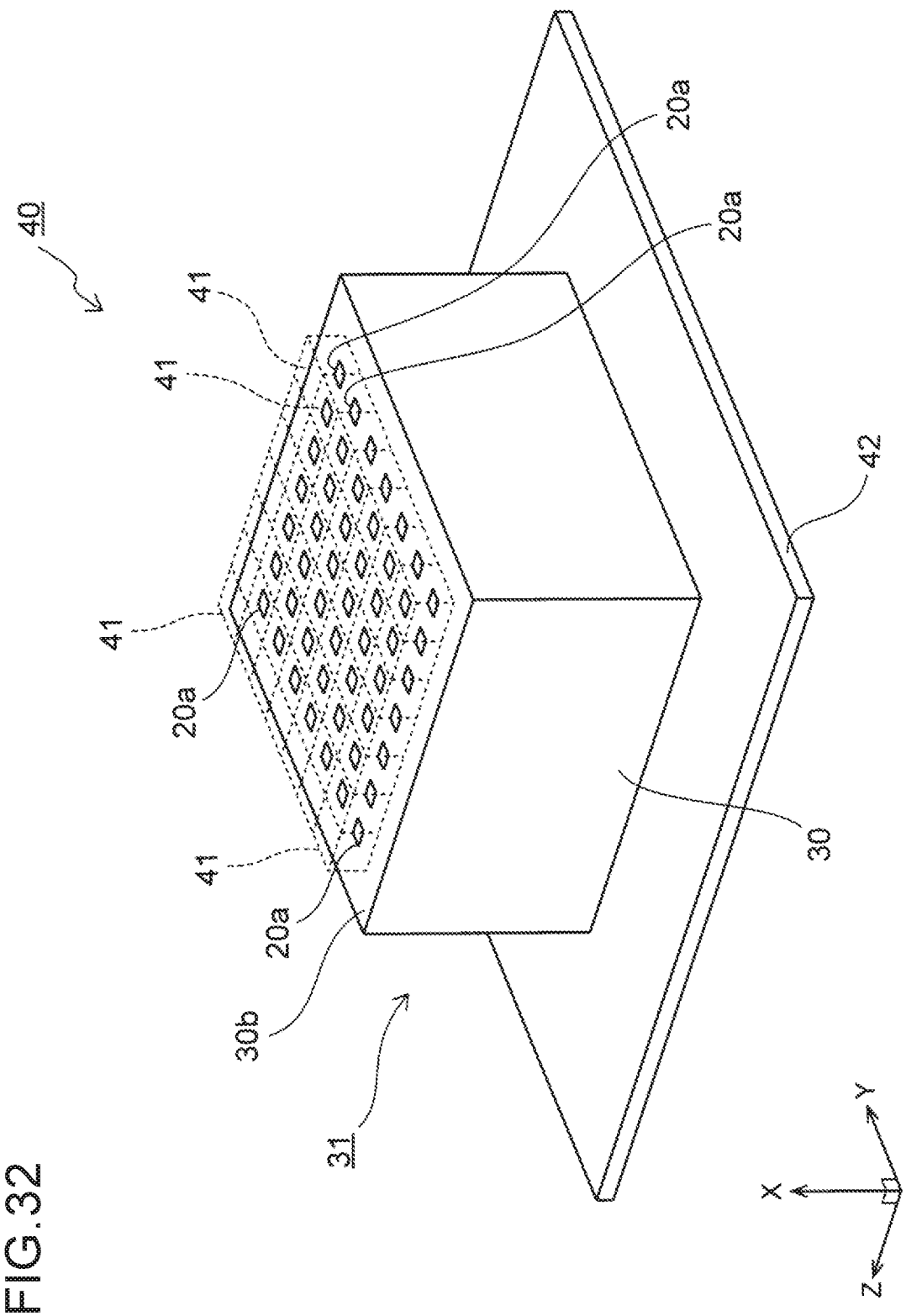

BACKING MEMBER AND ULTRASONIC PROBE INCLUDING LEADS AND SPACERS EMBEDDED IN A RESIN BODY

This application claims priority from Japanese Patent Application No. 2018-011897 filed on Jan. 26, 2018, the entire contents of which are herein incorporated by reference.

BACKGROUND

1. Technical Field

The present disclosure relates to a backing member and an ultrasonic probe.

2. Background Art

An ultrasonic diagnostic apparatus for acquiring an internal image of a subject using ultrasounds has come into wide use. In the ultrasonic diagnostic apparatus, ultrasounds generated by an ultrasonic probe are radiated onto the subject and echoes of the ultrasounds are captured by the ultrasonic probe so that an internal image of the subject can be acquired.

A sound absorbing material called backing member is provided in the ultrasonic probe. The backing member includes a large number of leads embedded in a sound-absorbing resin, and piezoelectric elements for generating the ultrasounds are connected to front ends of the leads. Thus, unnecessary ultrasounds can be absorbed by the backing member so that a pulse width of each of the ultrasounds radiated on the subject can be shortened. Accordingly, resolution of the image can be improved.

However, when the leads are embedded thus in the backing member, the leads may be bent during manufacturing, to thereby deteriorate reliability of the ultrasonic probe (see e.g., JP-A-2015-228932).

SUMMARY

Certain embodiments provide a backing member.
The backing member comprises:
a resin body comprising a lower surface and an upper surface opposite to each other;
a plurality of leads each of which extends in a first direction from the lower surface toward the upper surface, and that are embedded at pitches in the resin body; and
a plurality of insulating spacers each of which is provided between adjacent ones of the leads and extends in a second direction intersecting with the first direction, and that contact the leads.

Certain embodiments provide an ultrasonic probe.
The ultrasonic probe comprises:
a resin body comprising a lower surface and an upper surface opposite to each other;
a plurality of leads each of which extends in a first direction from the lower surface toward the upper surface, and that are embedded at pitches in the resin body;
a plurality of insulating spacers each of which is provided between adjacent ones of the leads and extends in a second direction intersecting with the first direction, and that contact the leads; and
a plurality of piezoelectric elements each of which is arranged on the upper surface and connected to a corresponding one of the leads exposed in the upper surface.

BRIEF DESCRIPTION OF THE DRAWINGS

FIG. 32 is a perspective view showing a positional relation between each of leads and each of piezoelectric elements in an ultrasonic probe according to the second embodiment.

DETAILED DESCRIPTION

A matter that has been studied by the present inventor will be described prior to description of embodiments of the present invention.

In this example, ultrasonic probes will be manufactured in the following manner.

Figure 1:
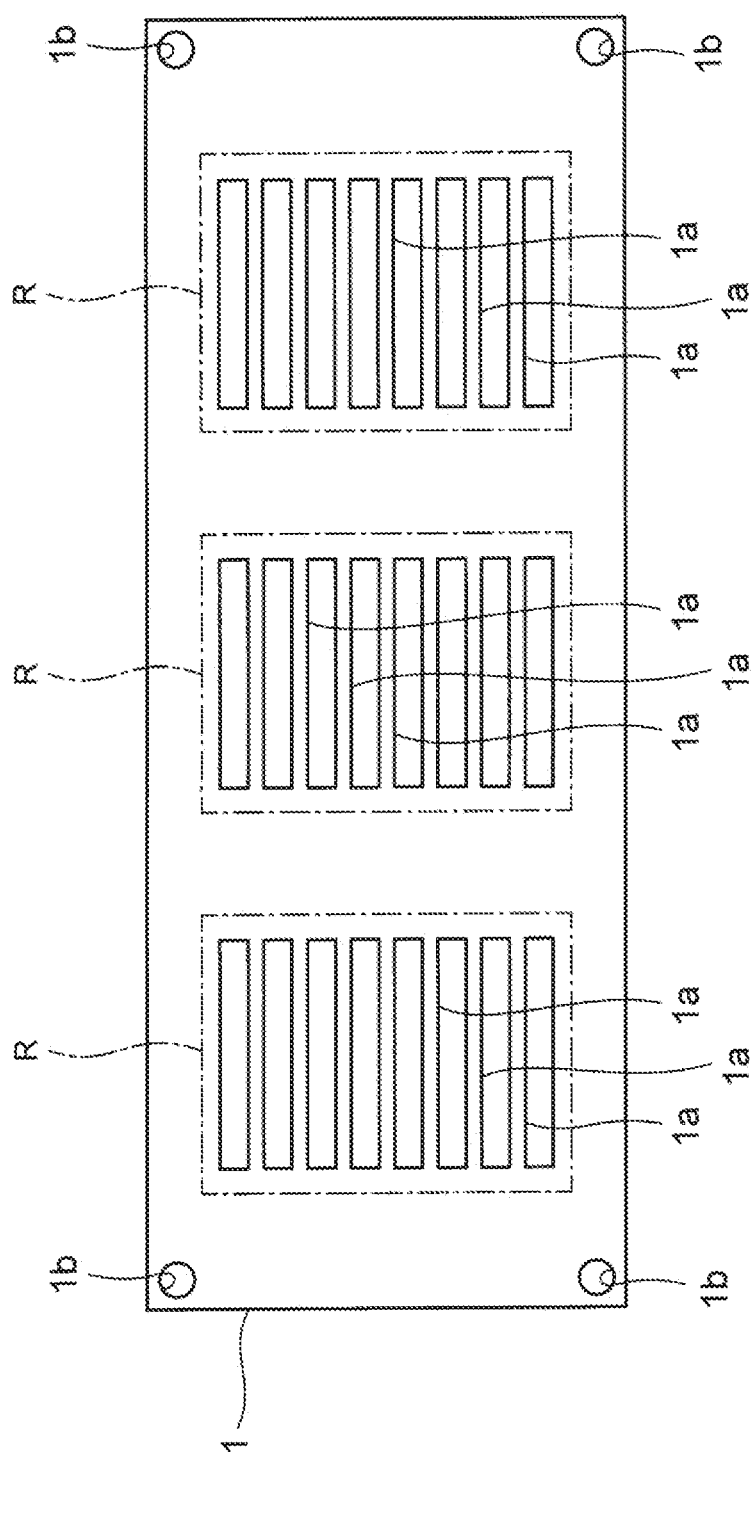
FIG. 1 is a plan view of a lead frame used for manufacturing ultrasonic probes.

FIG. 1 is a plan view of a lead frame used for manufacturing the ultrasonic probes.

The lead frame 1 is formed from a copper plate shaped like a rectangle long in an X direction. The lead frame 1 includes a plurality of product regions R. In each of the product regions R, a plurality of leads 1a are formed to extend in the X direction. The leads 1a are provided at pitches in a Y direction perpendicular to the X direction. Incidentally, a direction perpendicular to each of the X direction and the Y direction will be hereinafter set as Z direction.

In addition, holes 1b to be used for positioning later are formed in four corners of the lead frame 1.

Figure 2:
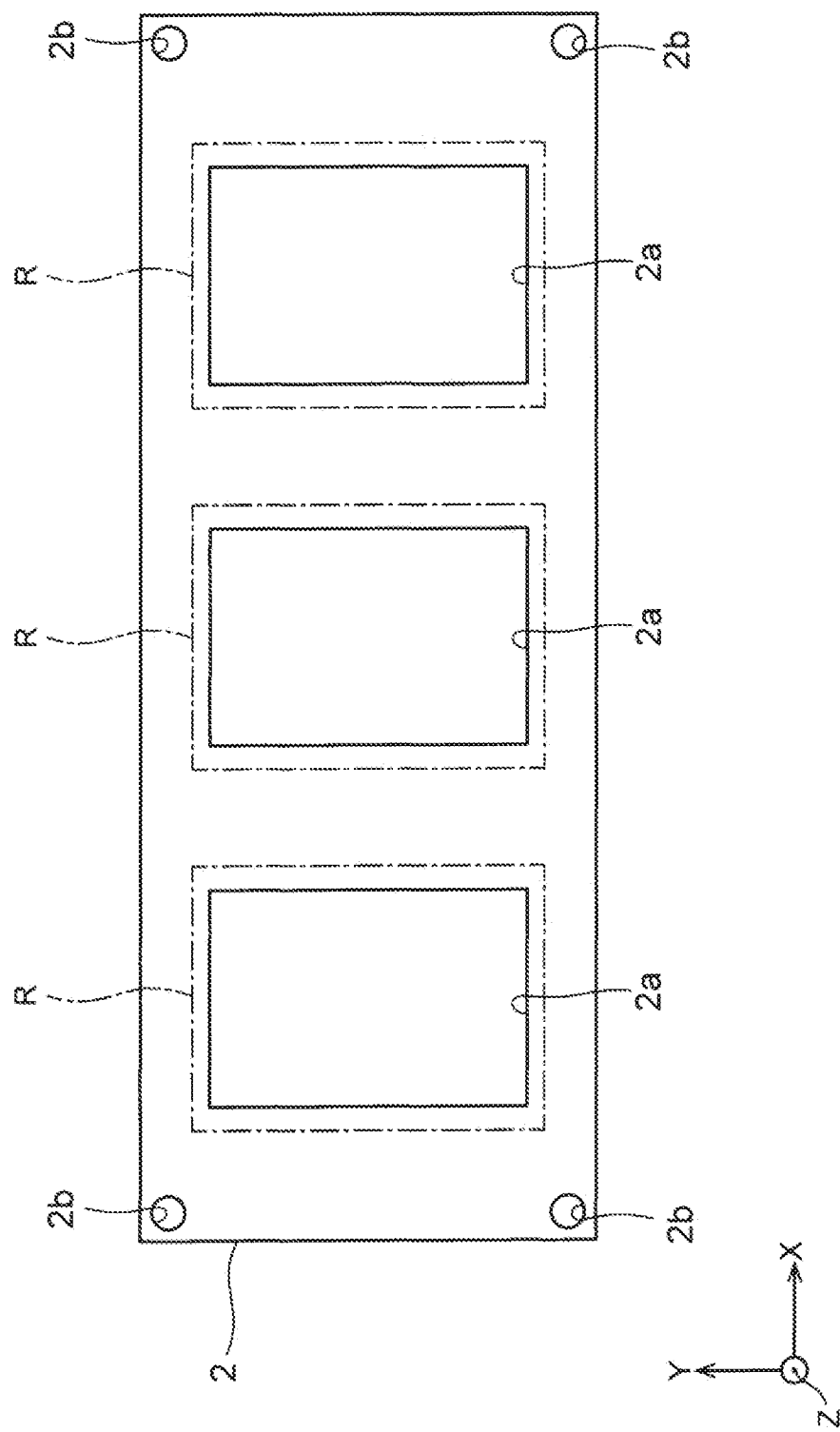
FIG. 2 is a plan view of a spacer member used together with the lead frame.

FIG. 2 is a plan view of a spacer member used together with the lead frame 1.

The spacer member 2 is made of a resin film of PET (polyethylene terephthalate) etc. shaped like a rectangle. A plurality of openings 2a corresponding to the product regions R are formed in the spacer member 2. Further, holes 2b corresponding to the holes 1b (see FIG. 1) of the lead frame 1 are formed in four corners of the spacer member 2.

By use of a plurality of such lead frames 1 and a plurality of such spacer members 2, ultrasonic probes are manufactured as follows.

FIGS. 3 to 6 are perspective views in process of manufacturing the ultrasonic probes using the lead frames 1 and the spacer members 2.

Figure 3:
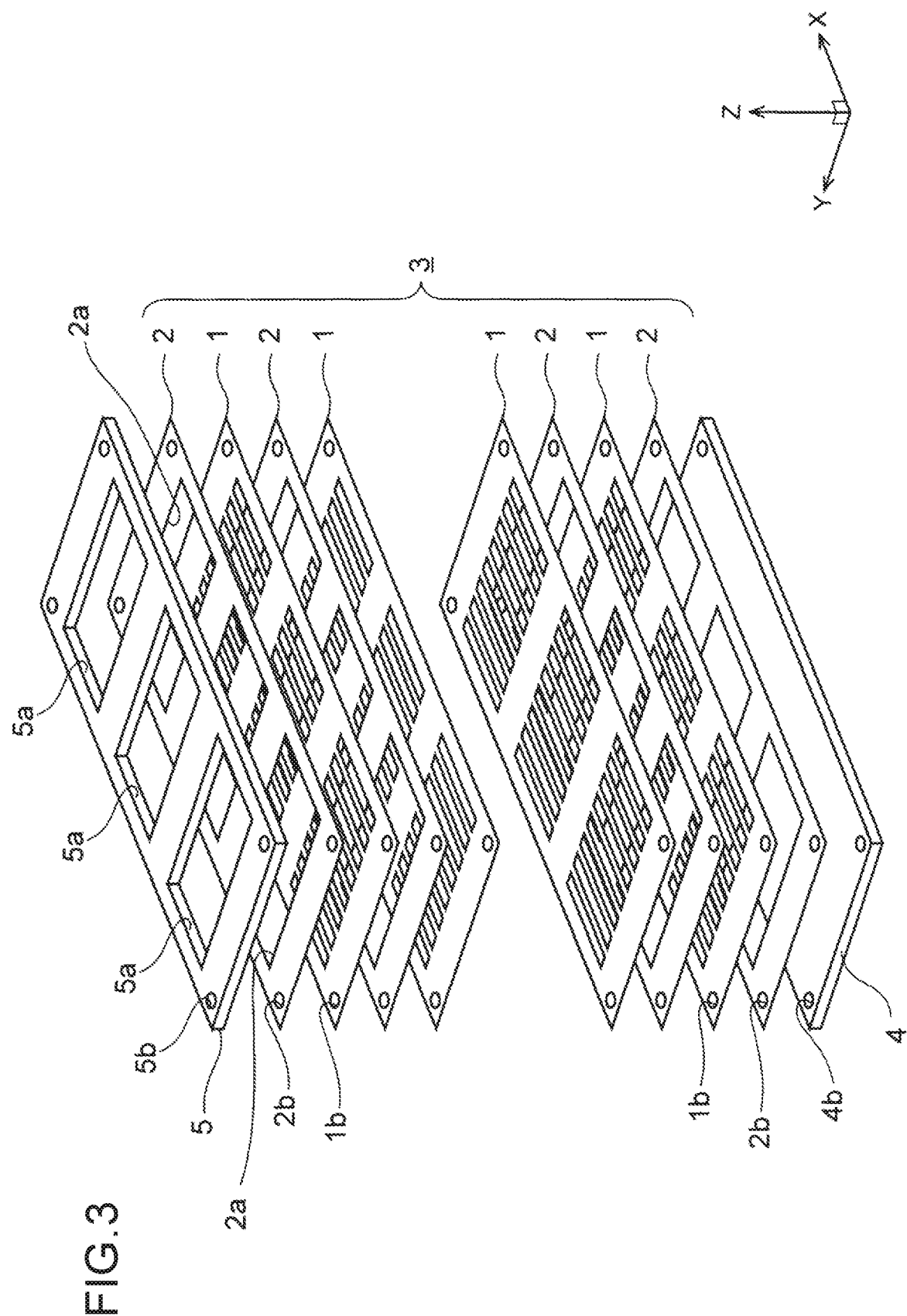
FIG. 3 is a perspective view in process of manufacturing ultrasonic probes using lead frames and spacer members (Part 1)

First, the lead frames 1 and the spacer members 2 are stacked on one another alternately to thereby form a stacked body 3 thereof, as shown in FIG. 3.

A lower support plate 4 is disposed on the bottom of the stacked body 3, and an upper support plate 5 is disposed on the top of the stacked body 3. Each of the lower support plate 4 and the upper support plate 5 is made of a metal plate of stainless steel etc. shaped like a rectangle similar to or the same as that of each of the lead frames 1.

Holes 4b and 5b overlapping with the aforementioned holes 1b and 2b respectively are provided in the support plates 4 and 5. Further, resin injection ports 5a overlapping with the openings 2a of the spacer members 2 are also provided in the upper support plate 5.

Figure 4:
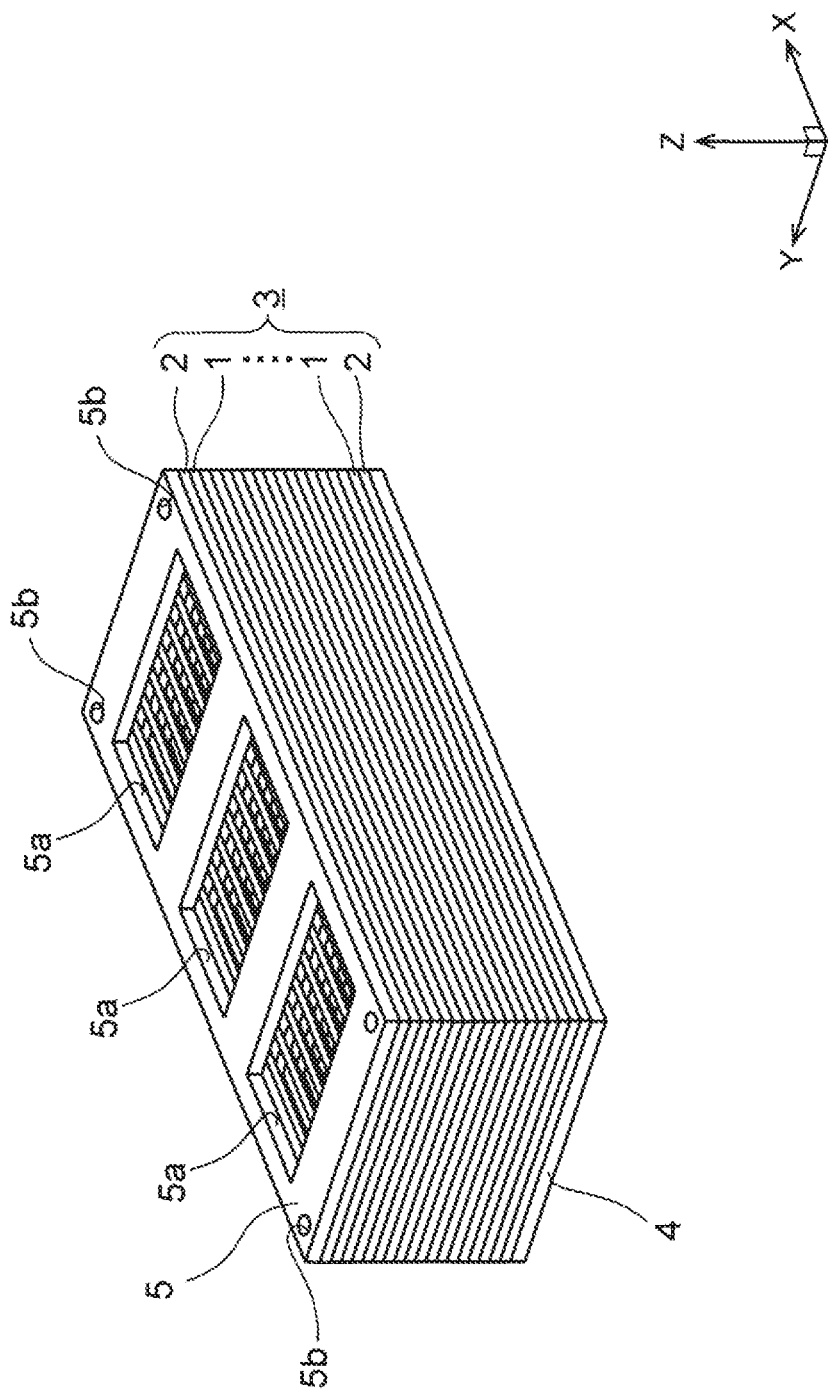
FIG. 4 is a perspective view in the process of manufacturing the ultrasonic probes using the lead frames and the spacer members (Part 2)

Next, the stacked body 3 is pressed from below and above by the lower support plate 4 and the upper support plate 5, as shown in FIG. 4. By not-shown pins inserted into the holes 5b on this occasion, the lead frames 1 and the spacer members 2 can be prevented from being displaced from one another while being pressed.

Figure 5:
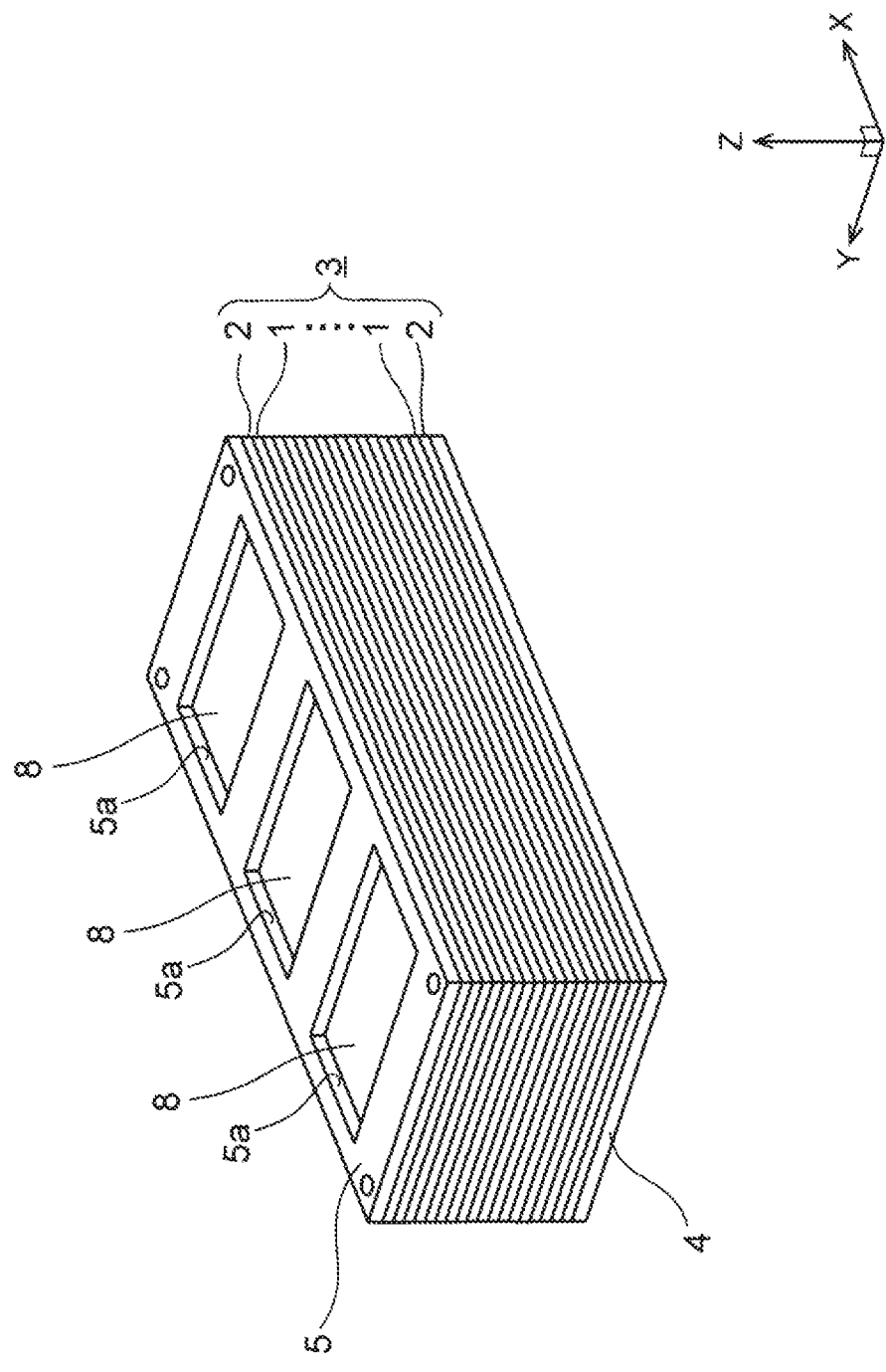
FIG. 5 is a perspective view in the process of manufacturing the ultrasonic probes using the lead frames and the spacer members (Part 3)

Next, a thermosetting resin is injected into the resin injection ports 5a of the upper support plate 5, and then, the resin is heated and thermally cured. As a result, resin bodies 8 are formed, as shown in FIG. 5.

Figure 6:
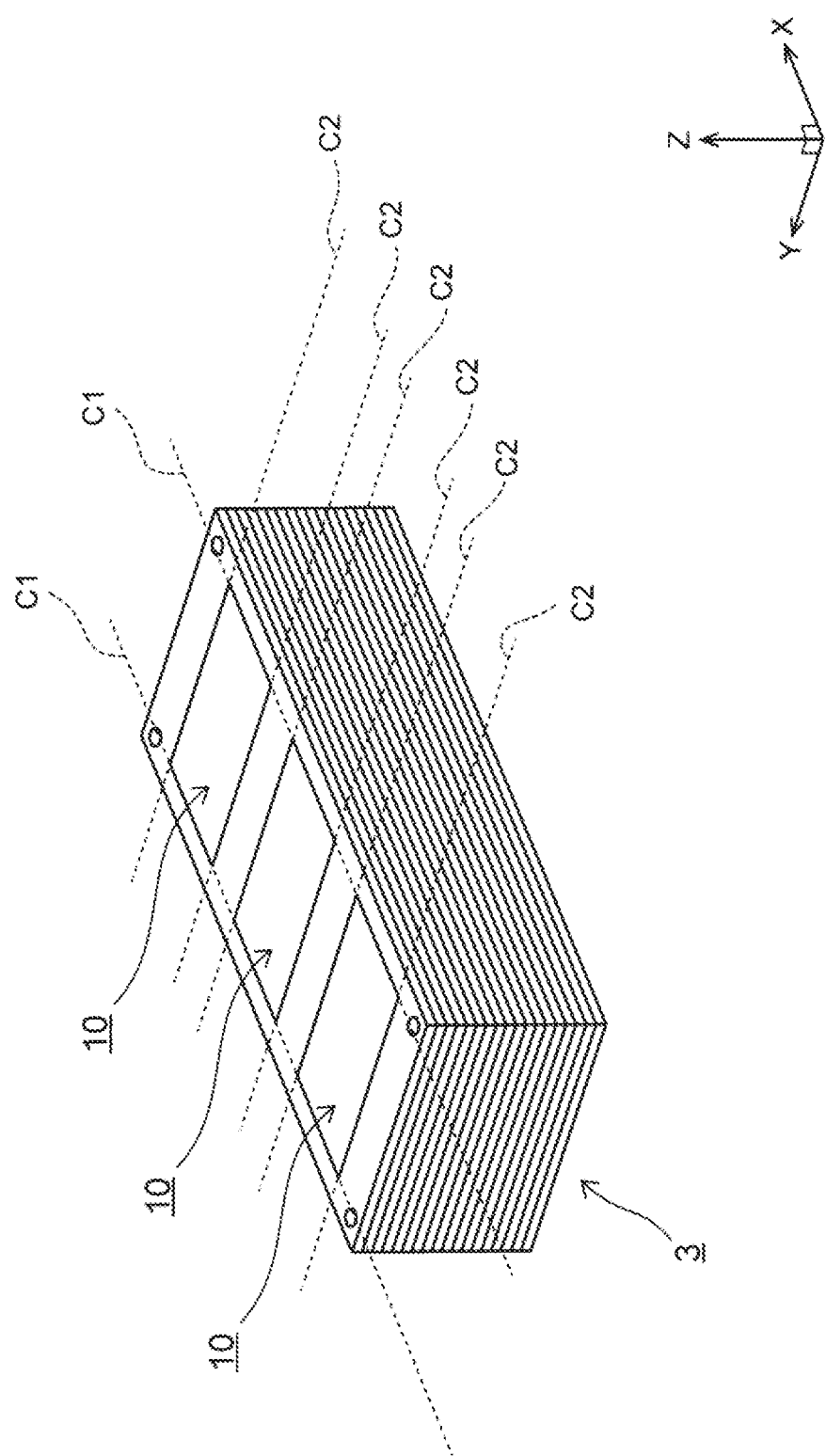
FIG. 6 is a perspective view in the process of manufacturing the ultrasonic probes using the lead frames and the spacer members (Part 4)

Successively, the stacked body 3 is extracted from a space between the lower support plate 4 and the upper support plate 5, as shown in FIG. 6. The stacked body 3 is cut along cutting lines C1 and C2 to be divided into individual pieces of backing members 10.

Figure 7:
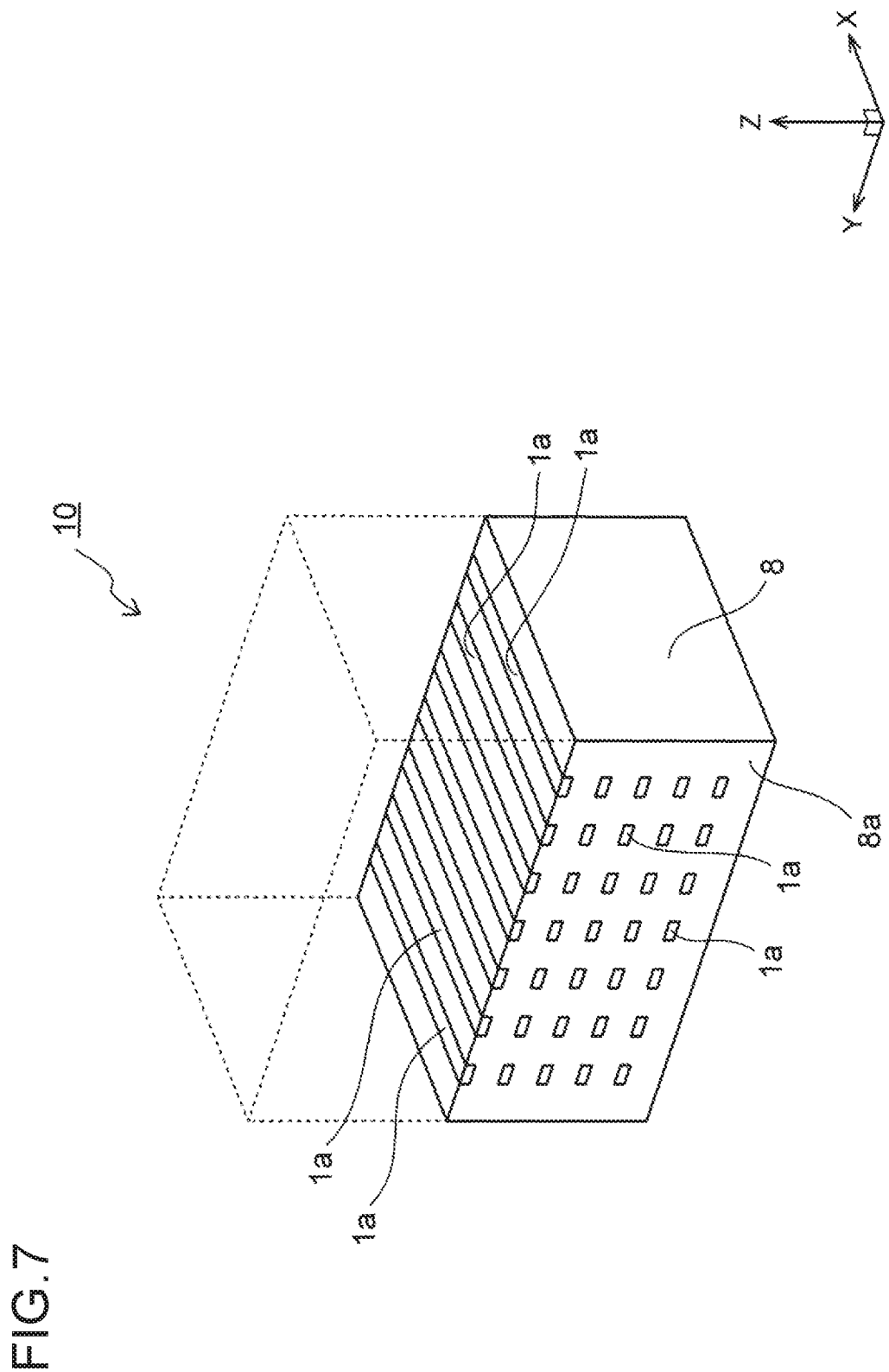
FIG. 7 is a perspective view of a backing member that has been used for study.

FIG. 7 is a perspective view of the backing member 10 obtained thus.

As shown in FIG. 7, the backing member 10 is provided with the resin body 8 shaped like a rectangular parallelepiped and the leads 1a embedded in the resin body 8. A lower surface 8a is formed in the resin body 8. End portions of the leads 1a are exposed from the lower surface 8a.

Next, an ultrasonic probe using the backing member 10 will be described.

Figure 8:
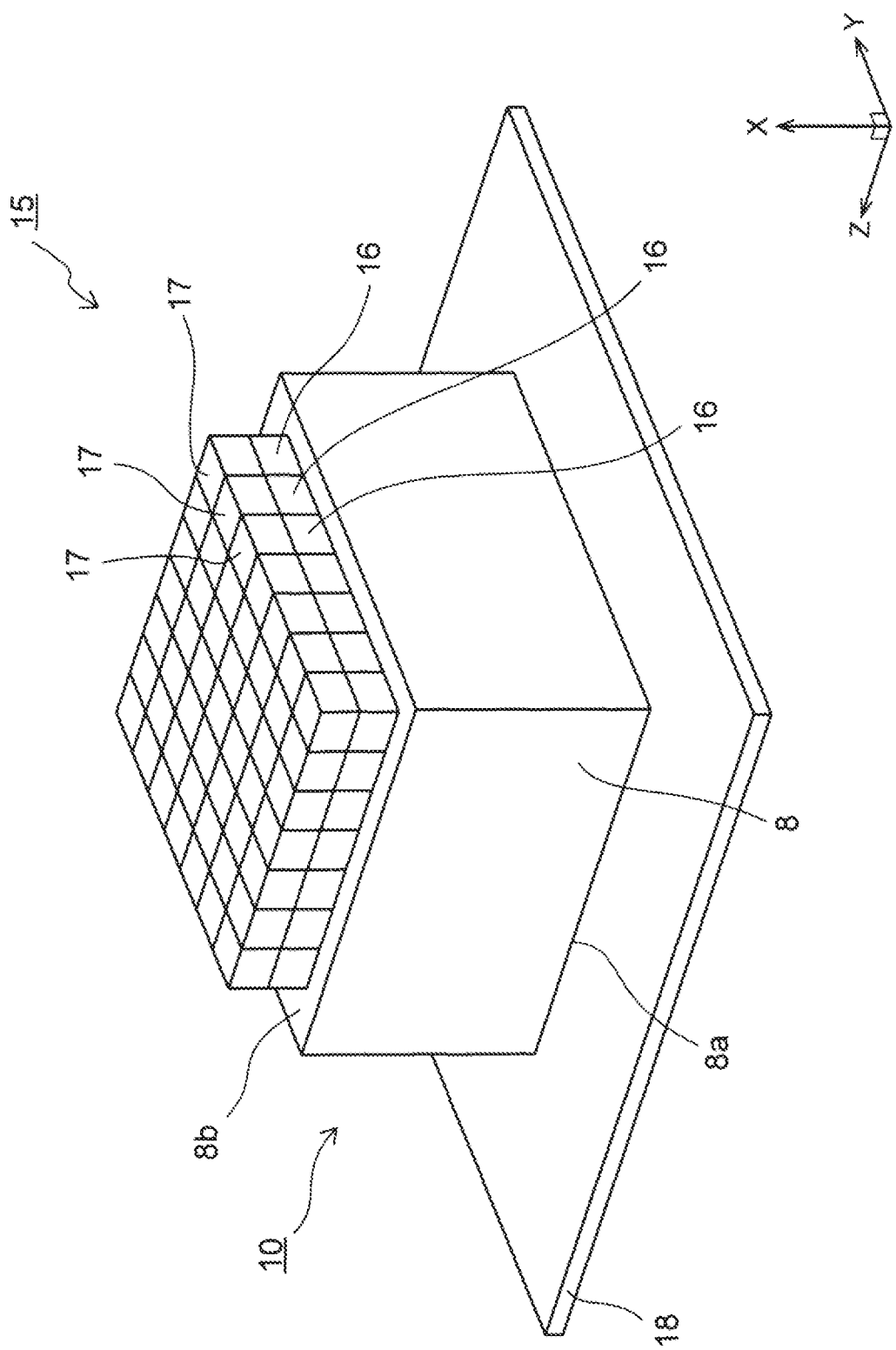
FIG. 8 is a perspective view of an ultrasonic probe that has been used for the study.

FIG. 8 is a perspective view of the ultrasonic probe that has been used for study.

The ultrasonic probe 15 is provided with the aforementioned backing member 10 and a plurality of piezoelectric elements 16.

In particular, the backing member 10 is fixedly bonded to a wiring substrate 18 with the lower surface 8a of the resin body 8 facing down. The piezoelectric elements 16 are arranged on an upper surface 8b opposite to the lower surface 8a. The piezoelectric elements 16 serve as elements that radiate ultrasounds onto a subject and receive echoes of the ultrasounds reflected on the subject.

An acoustic matching layer 17 made of a resin and serving for absorbing a difference of acoustic impedance between the subject and each of the piezoelectric elements 16 is provided on the piezoelectric element 16.

In such an ultrasonic probe 15, the ultrasounds generated by the piezoelectric elements 16 are absorbed by the resin body 8. Accordingly, unnecessary ultrasounds are not propagated to the wiring substrate 18. Further, due to the sound absorption made thus, a pulse width of each of the ultrasounds radiated on the subject can be shortened so that resolution of an image can be also improved.

Figure 9:
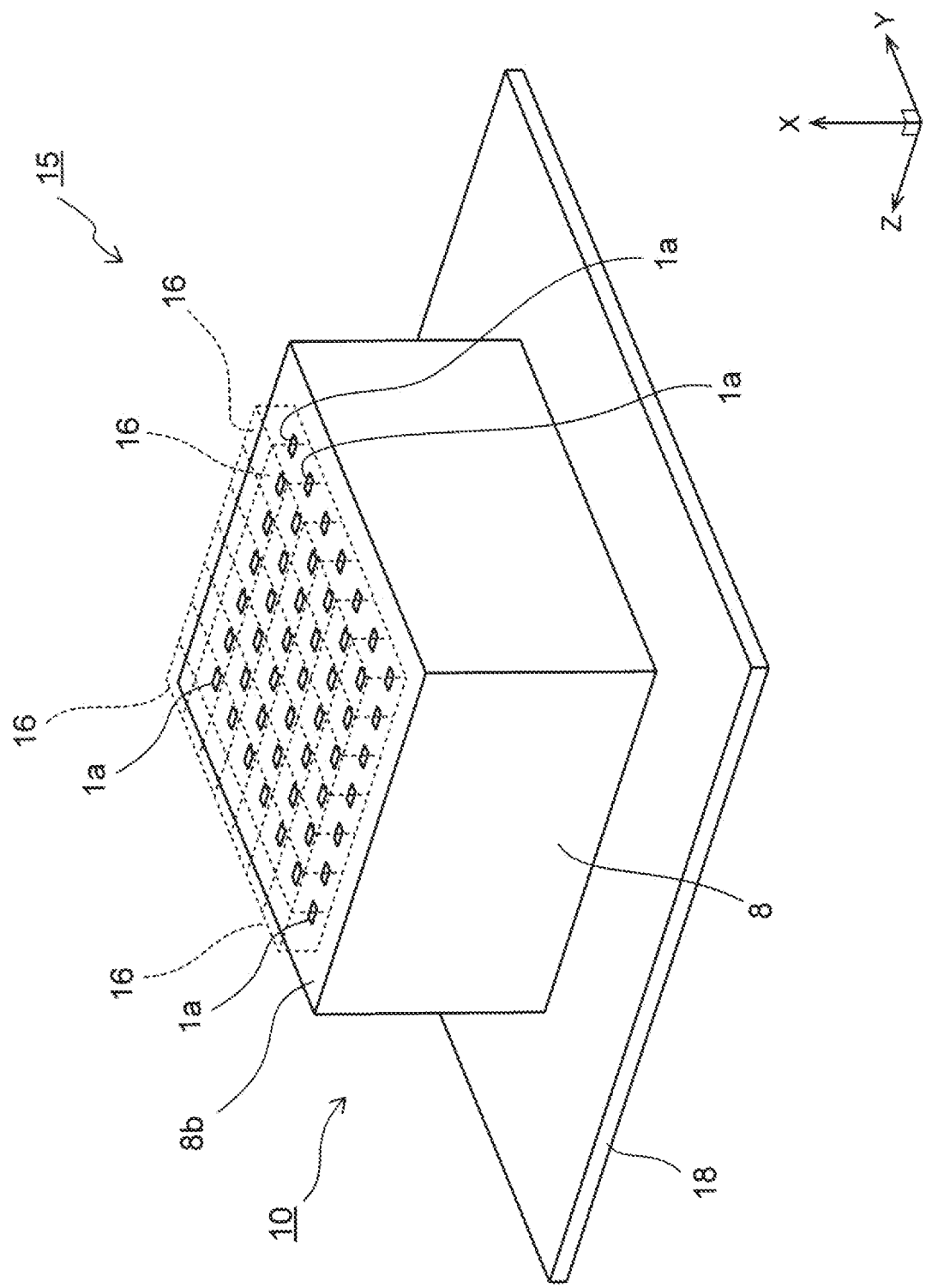
FIG. 9 is a perspective view showing a positional relation between each of leads and each of piezoelectric elements in the ultrasonic probe used for the study.

FIG. 9 is a perspective view showing a positional relation between each of the leads 1a and each of the piezoelectric elements 16.

As shown in FIG. 9, the leads 1a are exposed in the upper surface 8b of the resin body 8, and the piezoelectric elements 16 are provided on the leads 1a respectively. The leads 1a play roles of electrically connecting the piezoelectric elements 16 to the wiring substrate 18 respectively. Thus, signals can be exchanged between the piezoelectric elements 16 and the wiring substrate 18.

According to the ultrasonic probe 15 that has been described above, the resin is injected into the stacked body 3 constituted by the lead frames 1 and the spacer members 2, as shown in FIG. 5. Thus, a structure in which the leads 1a are embedded in each of the resin bodies 8 can be obtained easily.

However, according to research of the present inventor, it has been clear that the following problem arises in the ultrasonic probe 15.

Figure 10A:
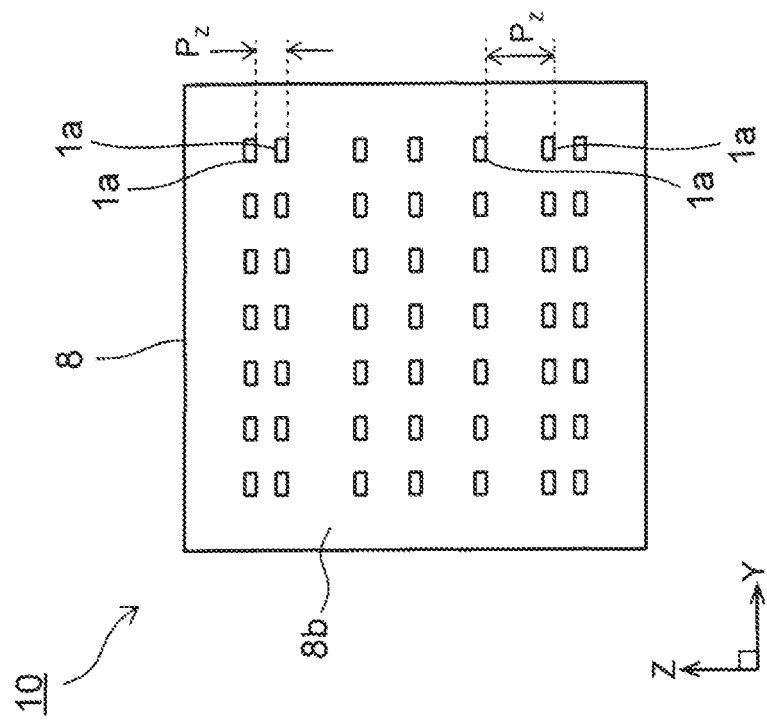
FIG. 10A is a top view of a good backing member.
Figure 10B:
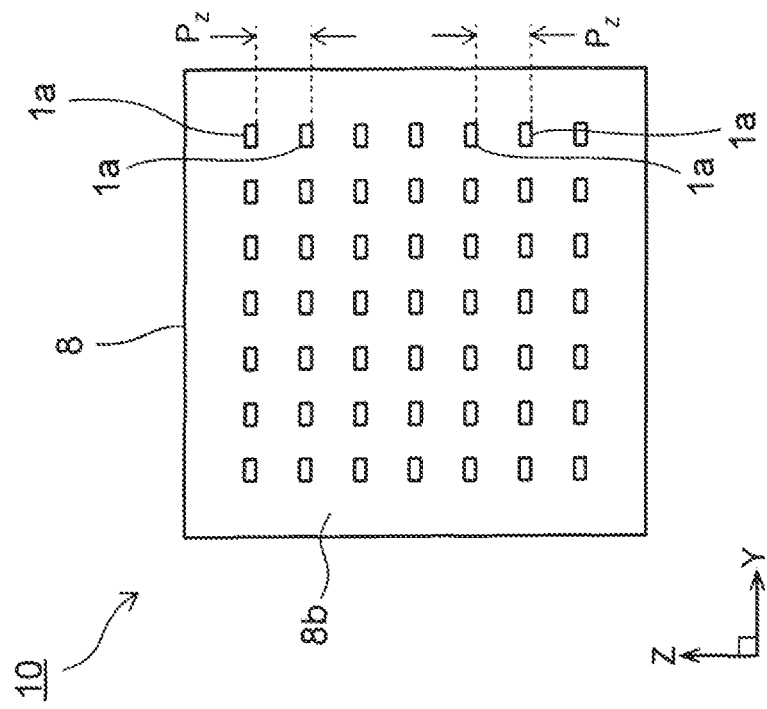
FIG. 10B is a top view of a defective backing member.

FIGS. 10A and 10B are top views of backing members for explaining this problem.

FIG. 10A is the top view of the good backing member 10 that has been manufactured normally without any problem.

In the backing member 10, the leads 1a are exposed at equal pitches in the upper surface 8b of the resin body 8, and Z-direction pitches $P_Z$ of all the leads 1a are the same.

On the other hand, FIG. 10B is the top view of the defective backing member 10.

In this example, Z-direction pitches $P_Z$ of the leads 1a are not uniform with one another to thereby create regions with a wide pitch $P_Z$ and regions with a narrow pitch $P_Z$. It is considered that the leads 1a are deformed by pressure when the resin is injected into the stacked body 3 in the step of FIG. 5 or by force when the resin is thermally cured and contracted.

When the pitches $P_Z$ are not uniform with one another in this manner, the leads 1a and the piezoelectric elements 16 (see FIG. 9) are displaced from each other respectively. Accordingly, it is difficult to excellently electrically connect the leads 1a and the piezoelectric elements 16 to each other respectively so that reliability of the ultrasonic probe 15 is deteriorated.

Moreover, when the leads 1a are deformed in the aforementioned manner, adjacent ones of the leads 1a contact each other to be electrically shirt-circuited. As a result, the reliability of the ultrasonic probe 15 is further deteriorated.

Respective embodiments in each of which reliability of an ultrasonic probe can be improved will be described below.

First Embodiment

Each of ultrasonic probes according to the present embodiment will be described while following a manufacturing process of the ultrasonic probes.

Figure 11:
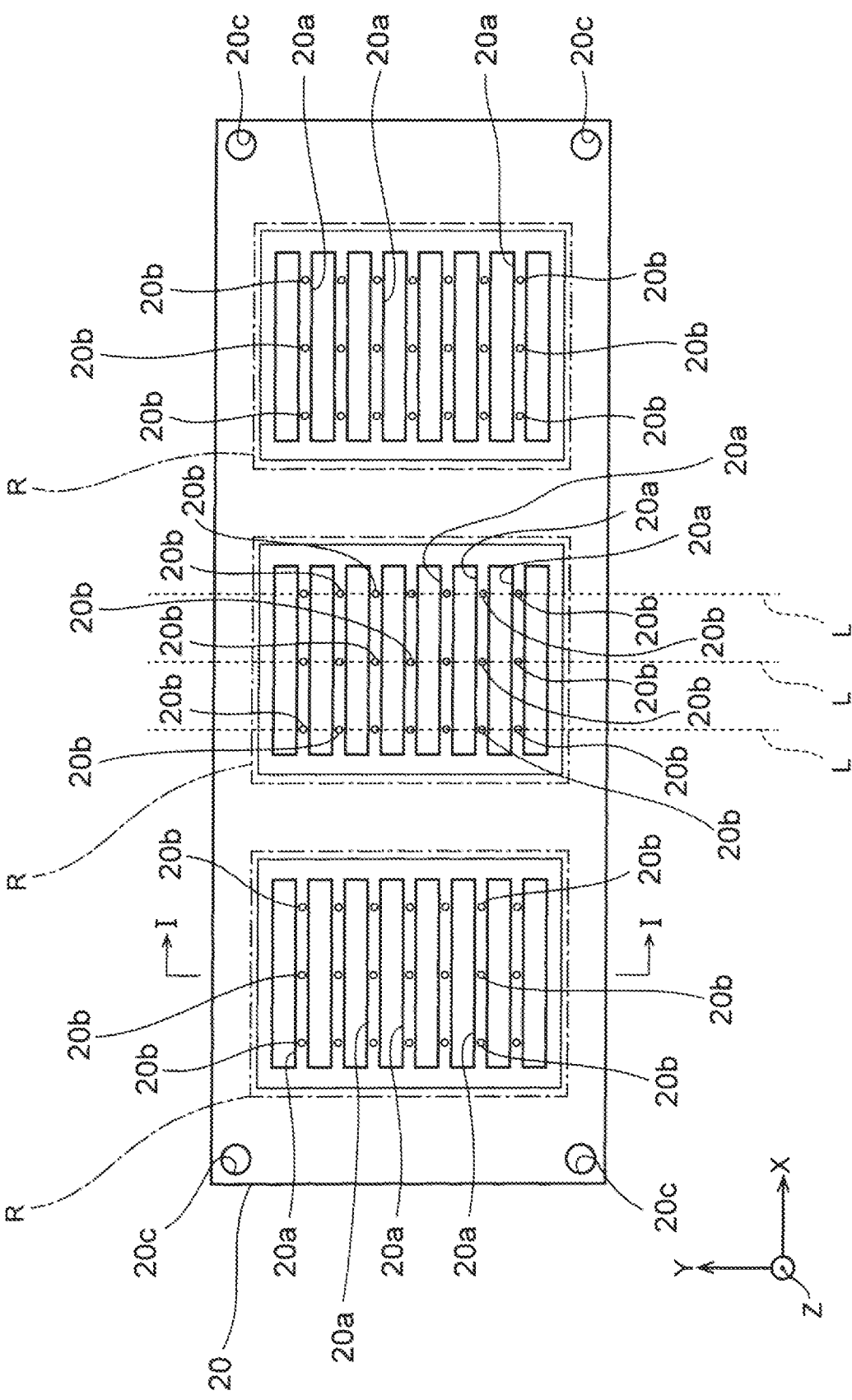
FIG. 11 is a plan view of a lead frame used in a first embodiment.

FIG. 11 is a plan view of a lead frame used in the present embodiment.

A copper plate is machined so that a lead frame 20 is manufactured. The lead frame 20 has a rectangular planar shape long in an X direction (first direction). Rectangular product regions R are defined in the lead frame 20. The product regions R serve as units in accordance with which the lead frame 20 will be divided into individual pieces later. In this example, in each of the product regions R, length of a short side is set at about 5 mm to about 50 mm and length of a long side is set at about 5 mm to about 150 mm.

A plurality of leads 20a extending in the X direction are formed in the product regions R. The leads 20a are formed at pitches in a Y direction (second direction). Further, a plurality of convex portions 20b protruding outward in a Z direction (third direction) are formed on front surfaces of the leads 20a.

In this example, the convex portions 20b are provided in rows along virtual straight lines L each extending in the Y direction, and the number of the rows of the convex portions 20b in one product region R is set at three. The planar shape of each of the convex portions 20b is not particularly limited. However, for example, the convex portion 20b may be formed into a circle with a diameter of about 5 μm to about 300 μm.

Further, holes 20c to be used for positioning are provided in four corners of the lead frame 20.

Incidentally, the description will be made below on the assumption that the X direction, the Y direction and the Z direction intersect with one another perpendicularly. However, any angle formed between adjacent ones of the X direction, the Y direction and the Z direction is not particularly limited as long as the X direction, the Y direction and the Z direction are directions intersecting with one another.

Figure 12:
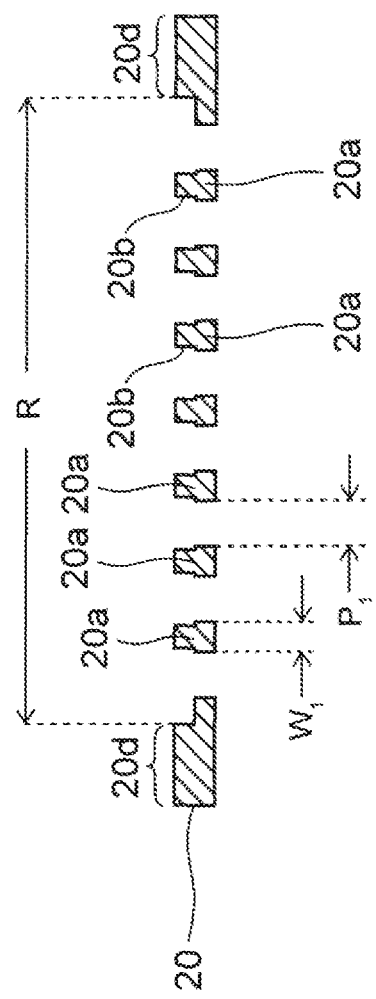
FIG. 12 is a sectional view taken along a line of FIG. 11.

FIG. 12 is a sectional view taken along a line 14 of FIG. 11.

As shown in FIG. 12, a thick portion 20d thicker in thickness than the inside of the product regions R is formed in the lead frame 20 outside the product regions R. Thus, rigidity of the lead frame 20 is enhanced so that handling of the lead frame 20 can be easy.

As an example, the thick portion 20d is about 150 μm thick. Each of the leads 20a inside each of the product regions R is about 50 μm thick. In addition, a protrusion amount of the convex portion 20b is about 100 μm from a front surface of the lead 20a. Incidentally, a total value of the protrusion amount of the convex portion 20b and the thickness of the lead 20a may be set to be equal to the thickness of the thick portion 20d.

A width $W_1$ or pitch $P_1$ of the leads 20a is also not particularly limited. For example, the width $W_1$ may be in a range of from 10 μm to one hundred and several ten μm, and the pitch $P_1$ may be about 300 μm.

Figure 13:
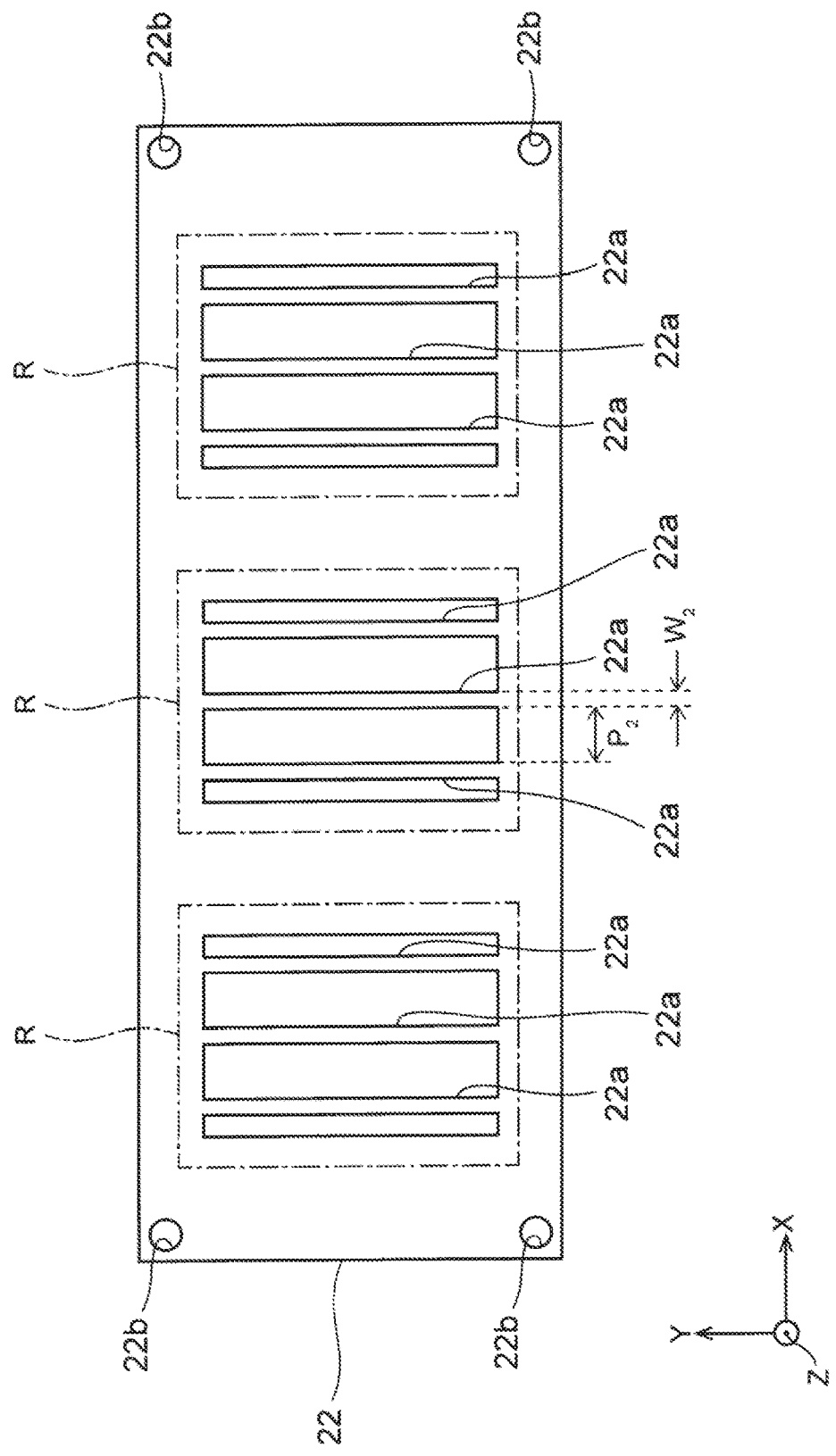
FIG. 13 is a plan view of a spacer member used in the first embodiment.

FIG. 13 is a plan view of a spacer member used together with the lead frame 20.

A resin sheet of PET etc. about 50 μm thick is machined into a rectangle that is long in the X direction in a similar manner to or the same manner as that of the lead frame 20 so that the spacer member 22 is manufactured. A plurality of beam-like insulating spacers 22a are formed in portions corresponding to each of the product regions R in the spacer member 22. Incidentally, only one insulating spacer 22a may be provided in one product region R.

The insulating spacers 22a extend in the Y direction and are formed at pitches in the X direction. As an example, a width $W_2$ of each of the insulating spacers 22a is about 0.1 mm to about 3 mm, and a pitch $P_2$ between adjacent ones of the insulating spacers 22a is about 0.1 mm or more.

Further, holes 22b corresponding to the holes 20c (see FIG. 11) of the lead frame 20 are formed in four corners of the spacer member 22.

Figure 14:
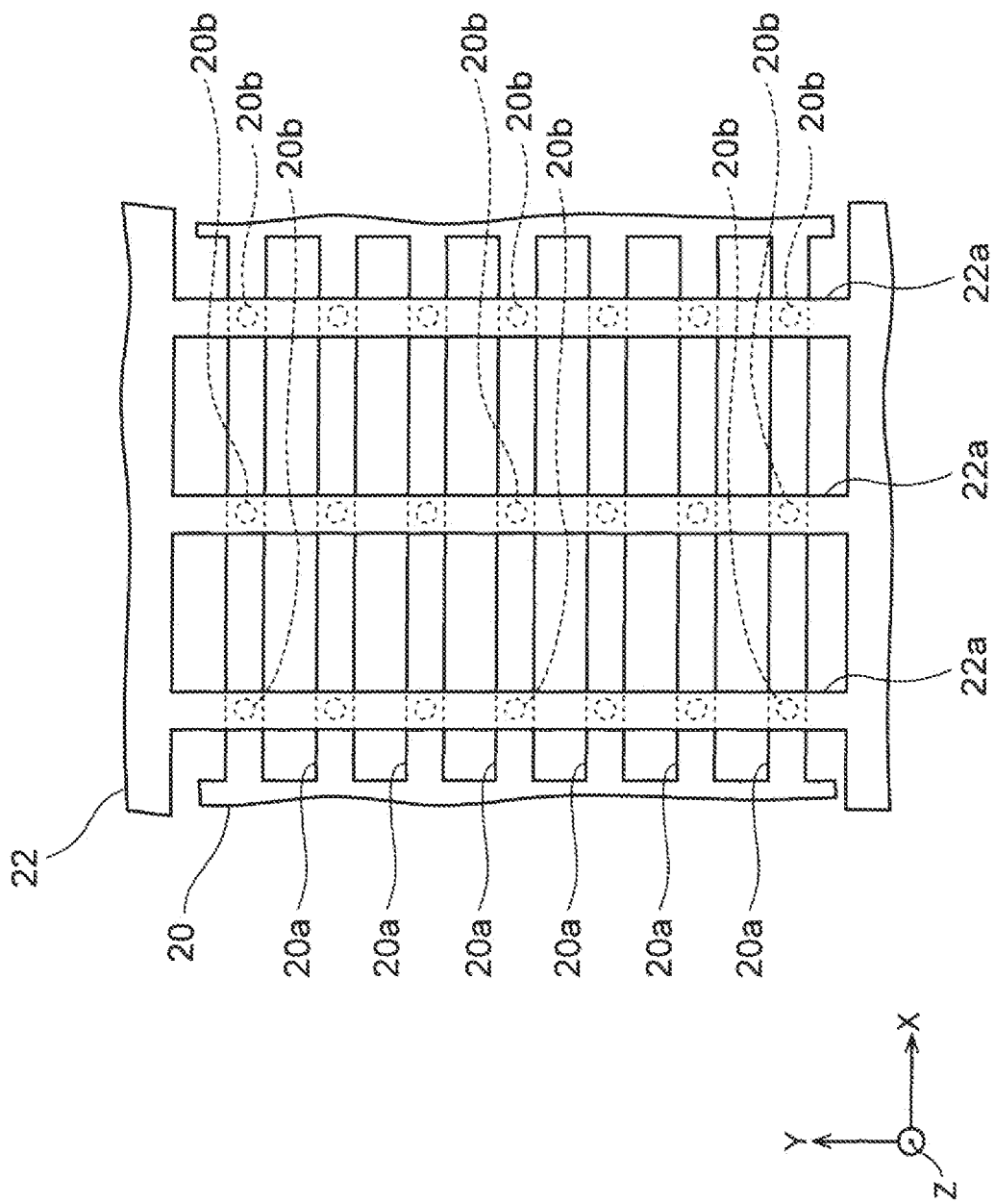
FIG. 14 is an enlarged plan view showing a positional relation between each of leads and each of insulating spacers in the first embodiment.

FIG. 14 is an enlarged plan showing a positional relation between each of the leads 20a and each of the insulating spacers 22a.

As shown in FIG. 14, the leads 20a and the insulating spacers 22a intersect with one another in plan view so that each of the convex portions 20b overlaps with a corresponding one of the insulating spacers 22a.

In the present embodiment, backing members will be manufactured in the following manner by use of a plurality of lead frames 20 formed in the aforementioned manner and a plurality of spacer members 22 formed in the aforementioned manner.

FIGS. 15 to 18 are perspective views in process of manufacturing the backing members according to the present embodiment.

Figure 15:
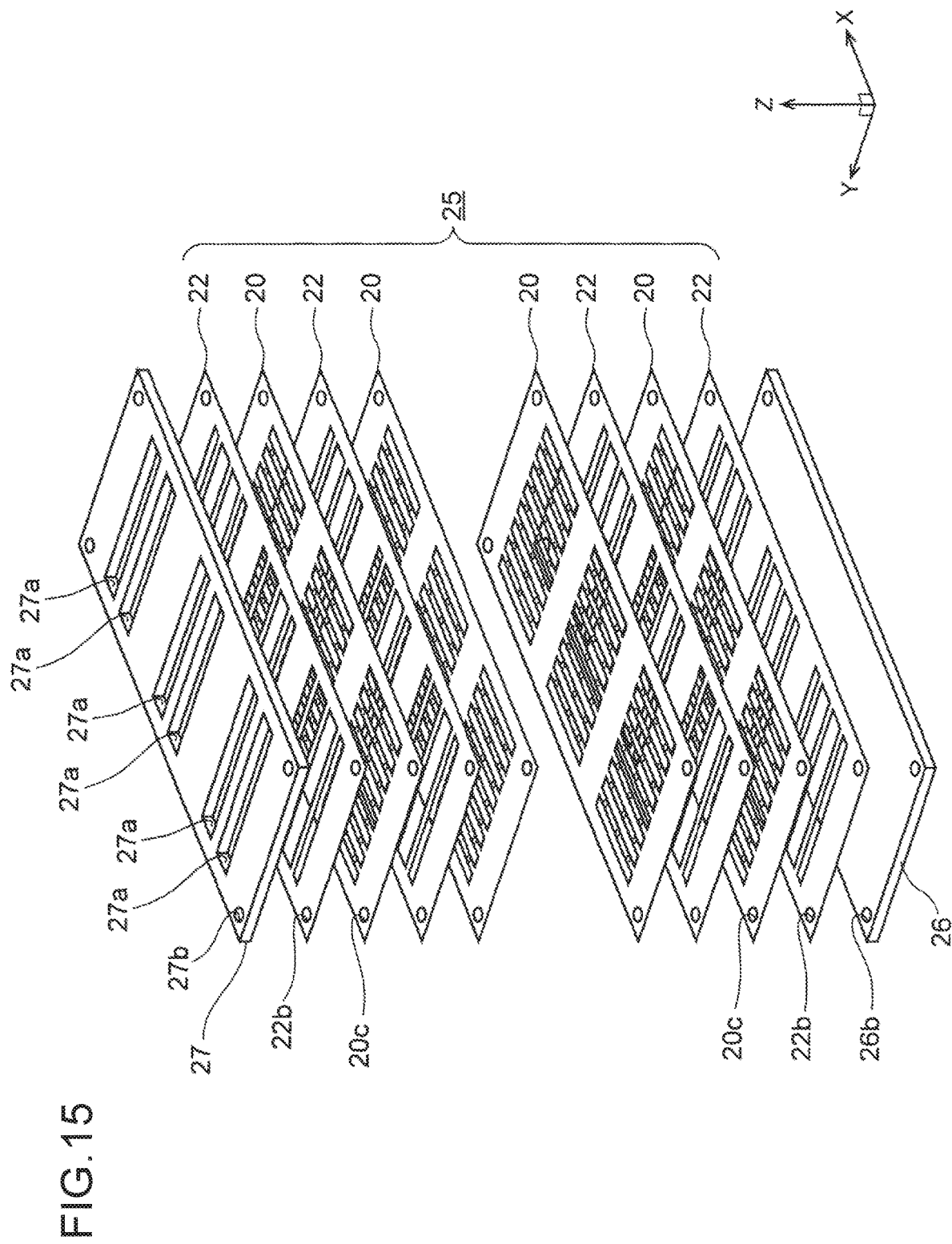
FIG. 15 is a perspective view in process of manufacturing backing members according to the first embodiment (Part 1)

First, as shown in FIG. 15, the lead frames 20 and the spacer members 22 are stacked on one another alternately to thereby manufacture a stacked body 25 thereof. Incidentally, both an uppermost layer and a lowermost layer in the stacked body 25 are the spacer members 22.

A lower support plate 26 is disposed on the bottom of the stacked body 25, and an upper support plate 27 is disposed on the top of the stacked body 25. Each of the lower support plate 26 and the upper support plate 27 is made of a metal plate of stainless steel etc. and shaped like a rectangle similar to or the same as that of each of the lead frames 20.

In addition, holes 26b and 27b overlapping with the aforementioned holes 20c and 22b are formed in the support plates 26 and 27 respectively. Further, resin injection ports 27a for injecting a resin later are also provided in the upper support plate 27.

Figure 16:
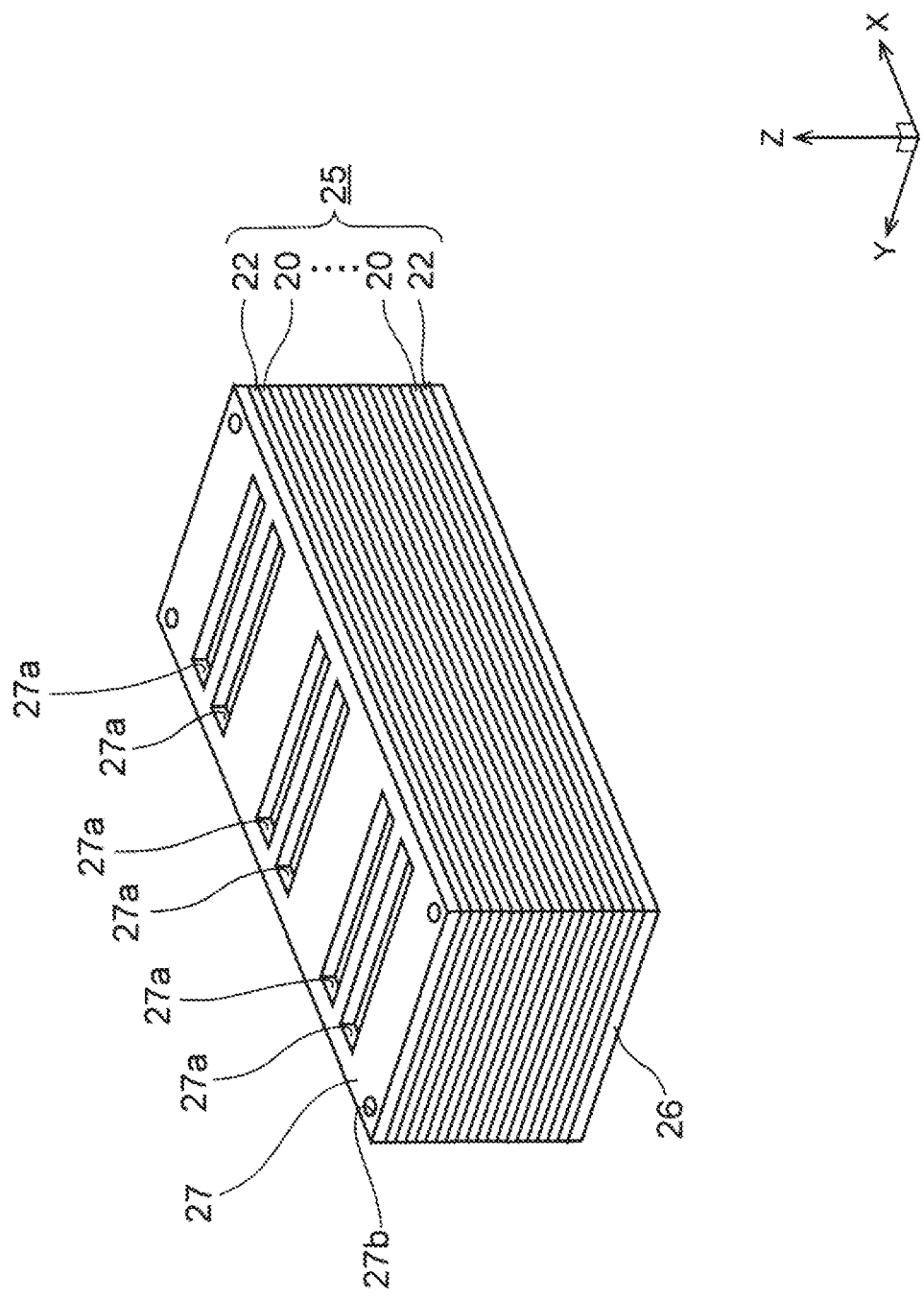
FIG. 16 is a perspective view in the process of manufacturing the backing members according to the first embodiment (Part 2)

Next, the stacked body 25 is pressed from below and above by the lower support plate 26 and the upper support plate 27, as shown in FIG. 16. By not-shown pins inserted into the holes 27b on this occasion, the lead frames 20 and the spacer members 22 can be prevented from being displaced from one another while being pressed.

Figure 19:
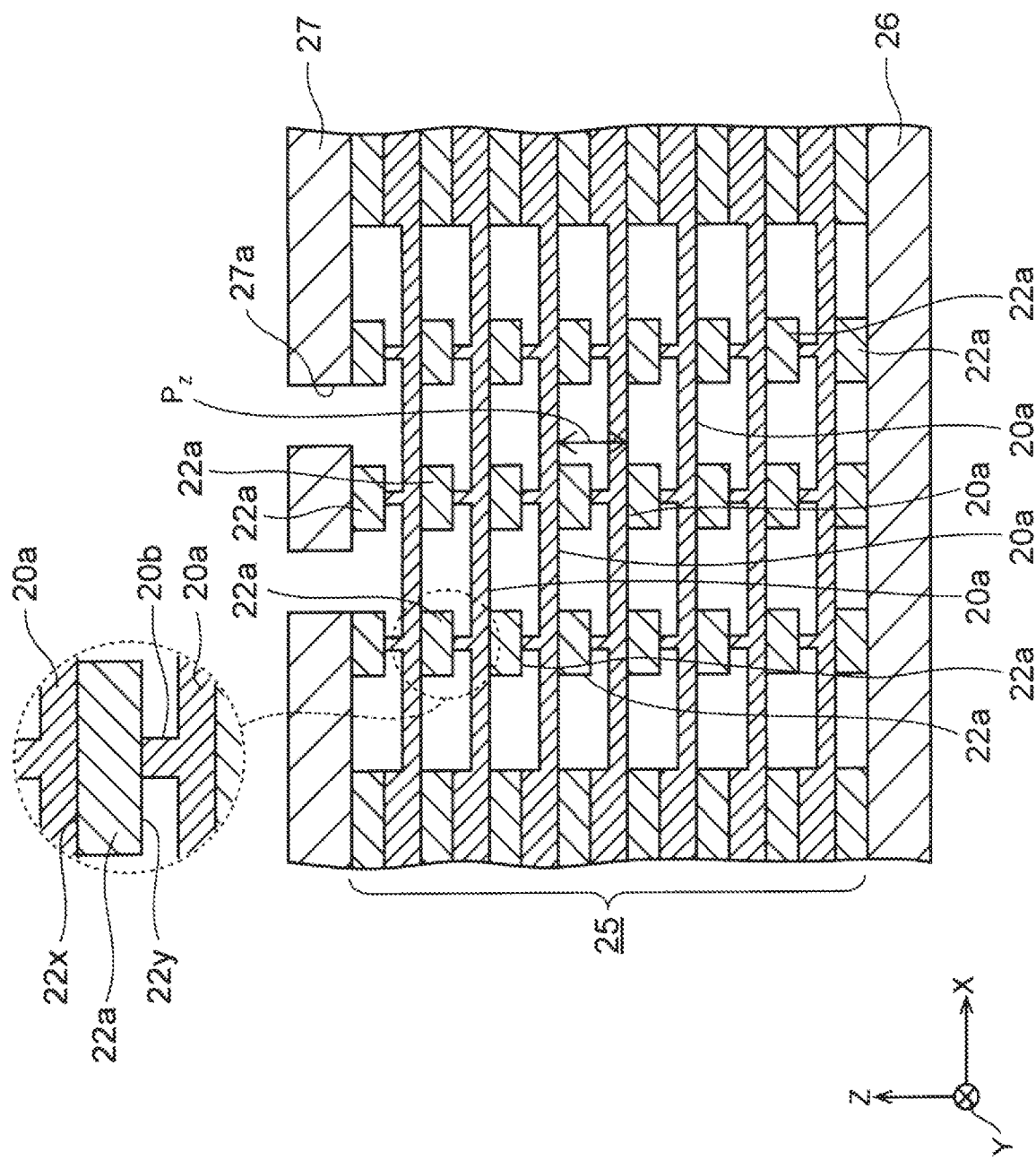
FIG. 19 is a sectional view in the process of manufacturing the backing members according to the first embodiment (Part 1)

FIG. 19 is a sectional view when the stacked body 25 in the present step has been cut along a plane parallel with an XZ plane.

As shown in a dotted line circle of FIG. 19, each of the insulating spacers 22a has a front surface 22x and a back surface 22y opposite to each other. Thus, the front surface 22x contacts corresponding ones of the leads 20a from below, and the back surface 22y contacts corresponding ones of the convex portions 20b located thereunder.

A resin such as PET that can be deformed slightly by pressure applied to the insulating spacer 22a is used as the material of the insulating spacer 22a. Therefore, the insulating spacer 22a can be crushed slightly by pressure applied thereto from the lower support plate 26 or the upper support plate 27. In the present step, the pressure may be adjusted to control a crushed amount of the insulating spacer 22a to thereby make a Z-direction pitch $P_Z$ of the leads 20a close to a designed value.

Figure 17:
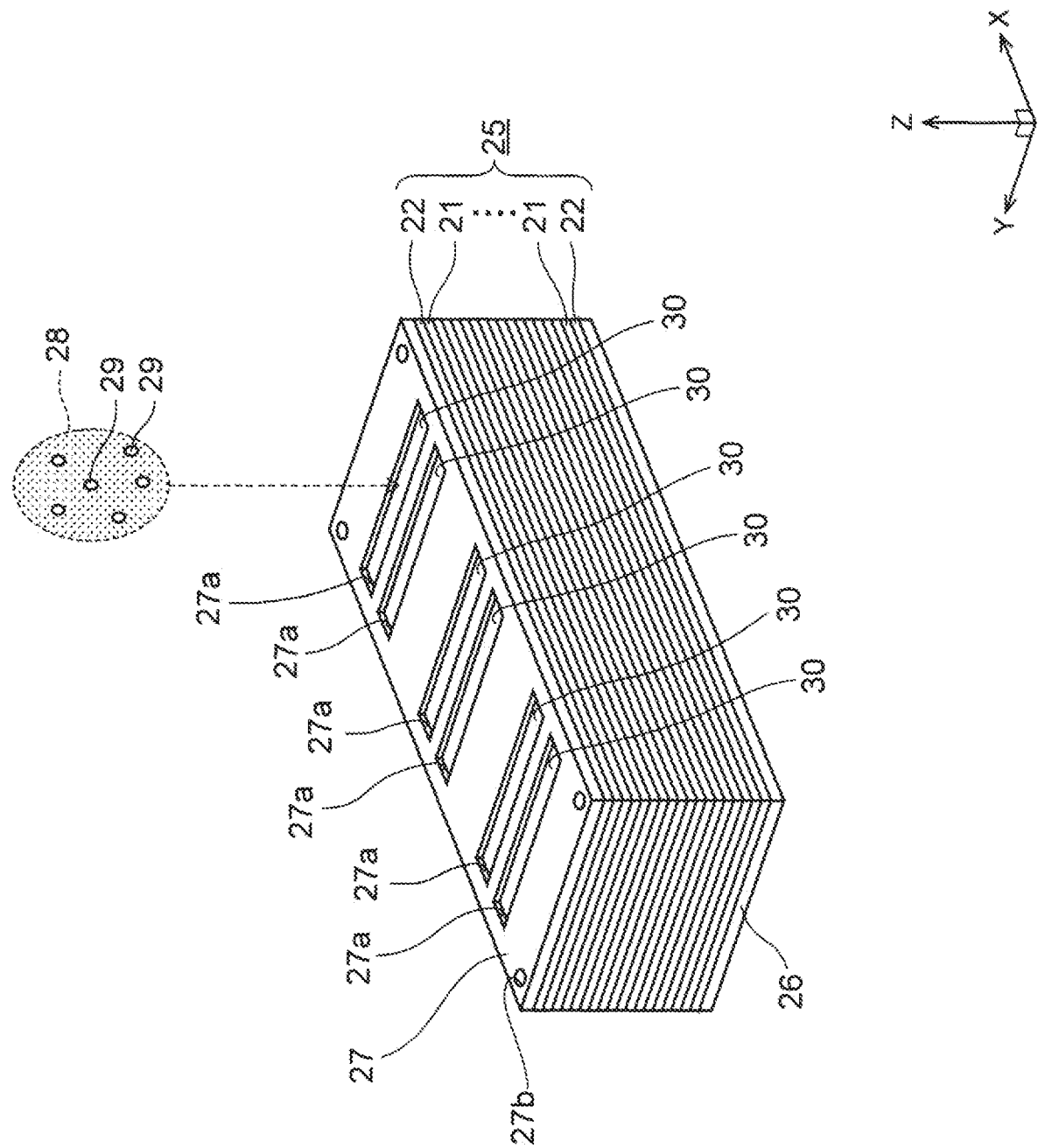
FIG. 17 is a perspective view in the process of manufacturing the backing members according to the first embodiment (Part 3)

Next, a thermosetting resin 28 is injected into the resin injection ports 27a of the upper support plate 27, as shown FIG. 17. The resin 28 is injected in a vacuum. Thus, bubbles generated inside the resin 28 during the injection can be degenerated.

Then, the resin 28 is heated and thermally cured. Thus, resin bodies 30 are formed inside the stacked body 25. The thermal curing is, for example, performed on conditions that heating temperature is 150° C. and heating time is two hours.

The resin 28 functions as a sound absorbing material absorbing ultrasound. In the present embodiment, a thermosetting epoxy resin containing fillers 29 is used as the resin 28.

Each of the fillers 29 is an additive for diffusing and attenuating the ultrasound in the resin 28 and adjusting acoustic impedance of the resin 28. Examples of such a filler 29 include a tungsten particle, an alumina particle, a hollow glass bead, etc. In addition, the particle size of the filler 29 is set as a particle size easy to diffuse the ultrasound. When a wavelength of the ultrasound in use is 5 MHz, an average particle size of the filler 29 is about 40 μm to about 80 μm.

Figure 20:
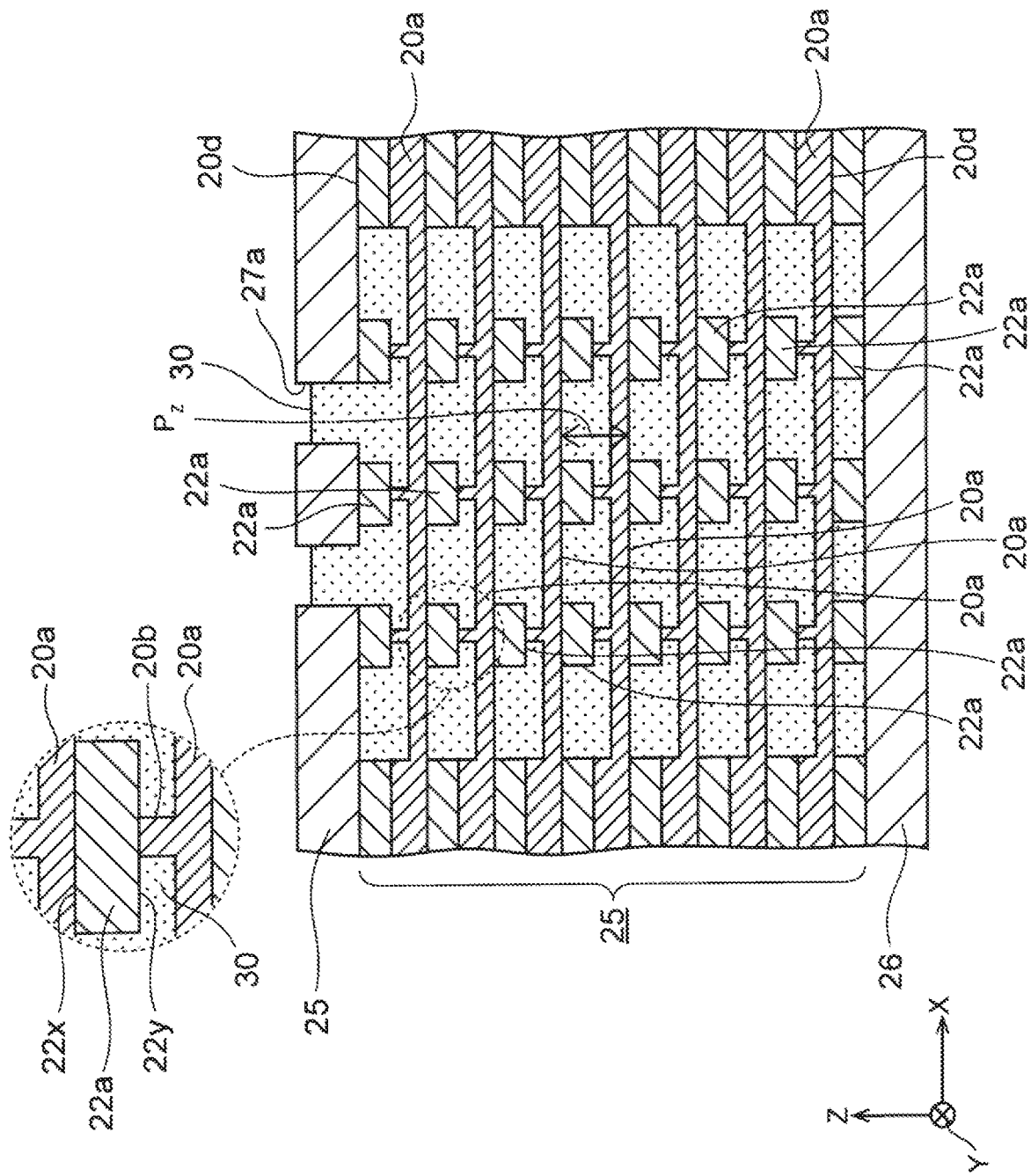
FIG. 20 is a sectional view in the process of manufacturing the backing members according to the first embodiment (Part 2)

FIG. 20 is a sectional view when the stacked body 25 in the present step has been cut along the plane parallel with the XZ plane.

As shown in a dotted line circle of FIG. 20, when the resin bodies 30 are formed, downward movement of the leads 20a is restricted by the insulating spacers 22a because the front surfaces 22x of the insulating spacers 22a contact the leads 20a from below. In addition, upward movement of the leads 20a is also restricted because the convex portions 20b of the leads 20a contact the back surfaces 22y of the insulating spacers 22.

As a result, the leads 20a can be suppressed from being deformed upward/downward by pressure when the resin 28 is supplied or by force when the resin 28 is thermally cured and contracted so that the pitch $P_Z$ of the leads 20a can be maintained at the designed value.

Particularly, in this example, the insulating spacers 22a are provided at pitches in the X direction. Accordingly, the deformation of the leads 20a can be effectively restricted by the insulating spacers 22a.

Moreover, the leads 20a are formed to be thinner than thick portion 20d, and parts contacting the back surfaces of the insulating spacers 22a are limited to only the convex portions 20b. Accordingly, the fillers 29 (see FIG. 17) can be hardly hindered from flowing inside the resin 28 by the leads 20. Thus, the fillers 29 can be uniformly dispersed in the resin 28 so that acoustic impedance of each of the resin bodies 30 can be uniform.

In addition, due to each of the convex portions 20b shaped like a circle in plan view as in the present embodiment, the fillers 29 can smoothly flow around the convex portions 20b. Accordingly, a distribution of the fillers 29 in the resin 28 can be made further uniform.

Further, each of the leads 20a is thinned as described above. Thus, the ultrasound is hardly prevented from being propagated through the lead 20a. Accordingly, a sound absorbing effect of each backing member can be also enhanced.

Figure 18:
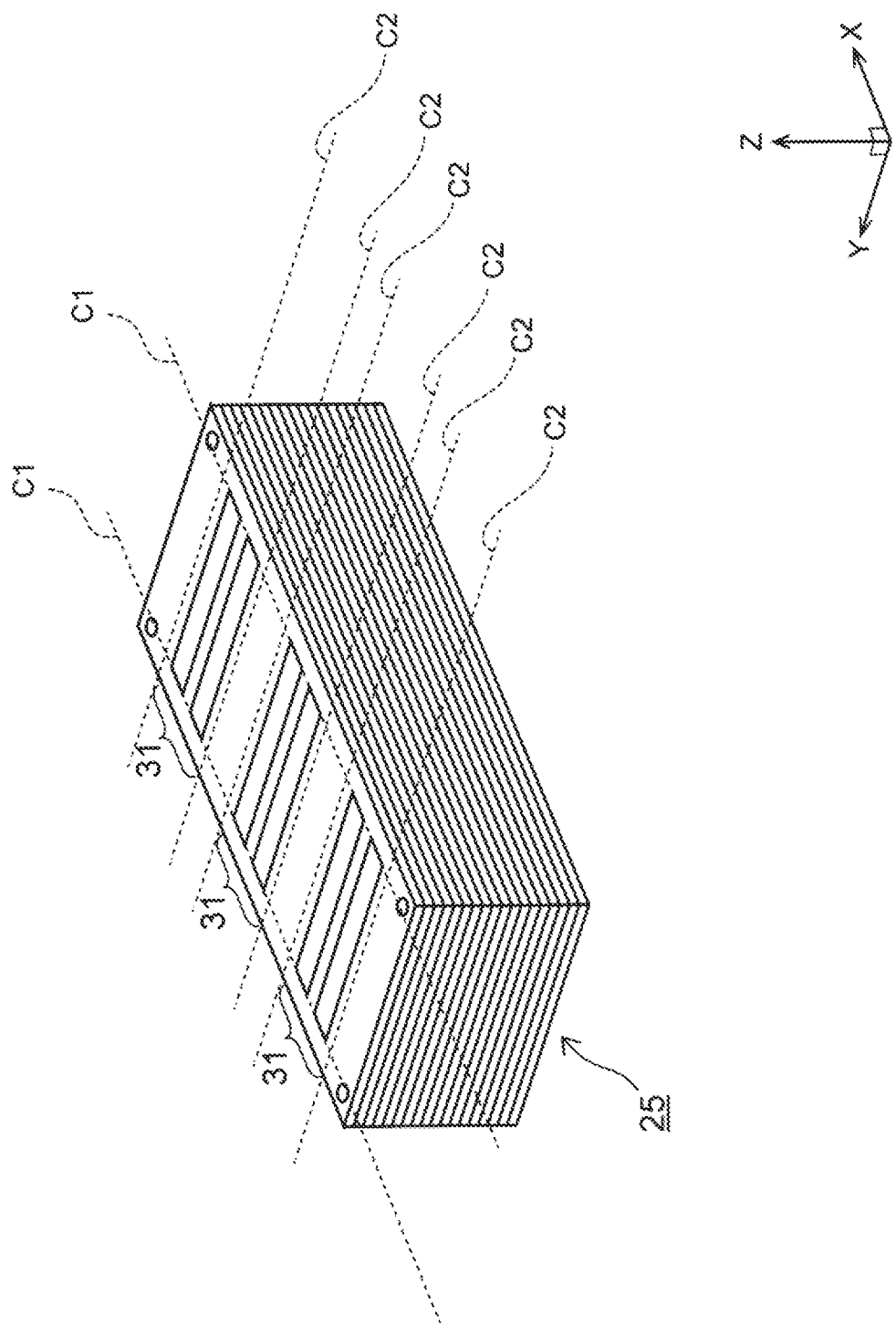
FIG. 18 is a perspective view in the process of manufacturing the backing members according to the first embodiment (Part 4)

Next, the stacked body 25 is extracted from a space between the lower support plate 26 and the upper support plate 27, as shown in FIG. 18. The stacked body 25 is cut along cutting lines C1 and C2 to be divided into individual pieces of backing members 31.

Figure 21:
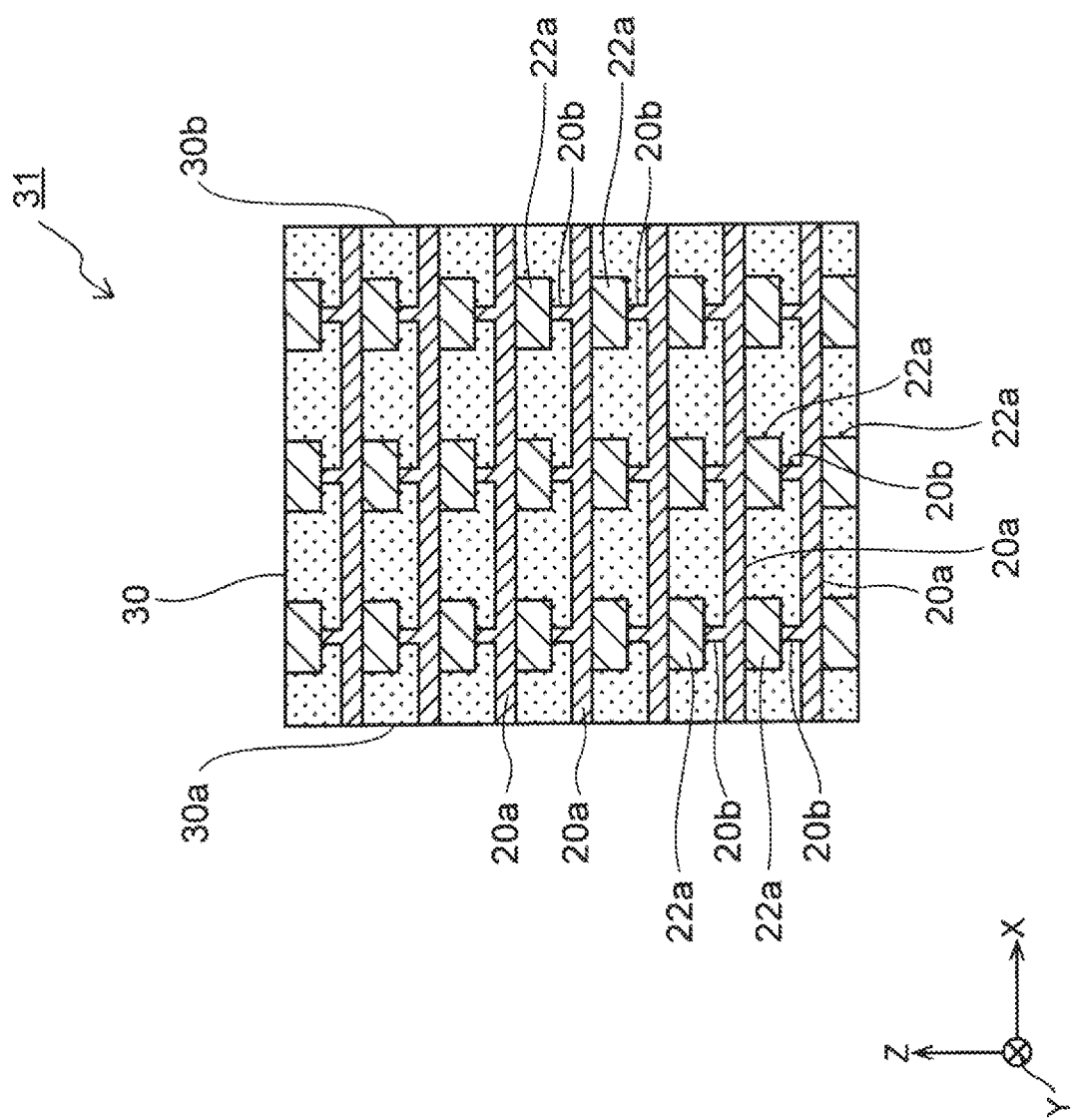
FIG. 21 is a sectional view in the process of manufacturing the backing members according to the first embodiment (Part 3)

FIG. 21 is a sectional view when any of the thus obtained backing members 31 is cut along the plane parallel with the XZ plane.

As shown in FIG. 21, the leads 20a and the insulating spacers 22a are embedded in the resin body 30. In particular, each of the insulating spacers 22a is provided between ones of the leads 20a adjacent to each other in the Z direction. In addition, a lower surface 30a and an upper surface 30b opposite to each other are formed in the resin body 30. End portions of the leads 20a are exposed from each of the lower surface 30a and the upper surface 30b.

Incidentally, the thick portion 20d (see FIG. 12) has been removed by the step of division into the individual pieces in this example. However, the thick portion 20d may be partially left on ones of the end portions of the leads 20a in advance so that the thick portion 20d can be exposed from the lower surface 30a or the upper surface 30b.

Figure 22:
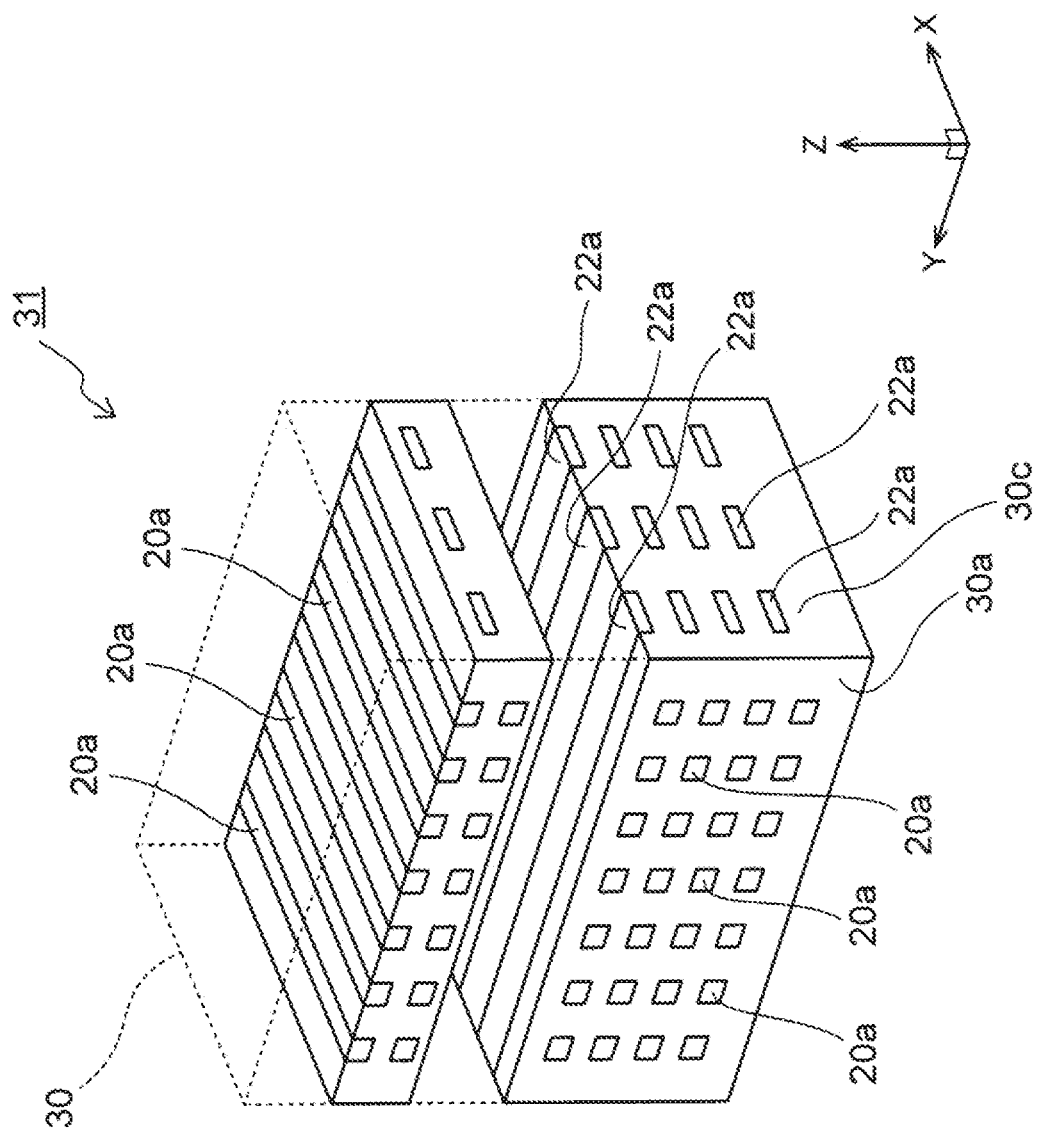
FIG. 22 is a perspective view of the backing member according to the first embodiment.

FIG. 22 is a perspective view of the backing member 31.

As shown in FIG. 22, the resin body 30 is shaped like a rectangular parallelepiped by the step of division into the individual units, and end portions of the insulating spacers 22a are exposed in a side surface 30c of the resin body 30. The insulating spacers 22a are embedded in the resin body 30 so that the insulating spacers 22a are provided at pitches in each of the X direction and the Z direction and extend in the Y direction.

Incidentally, illustration of some of the insulating spacers 22a is omitted from FIG. 22.

On the other hand, the leads 20a are embedded in the resin body 30 so that the leads 20a are provided at pitches in each of the Y direction and the Z direction and extend in the Y direction.

Figure 23:
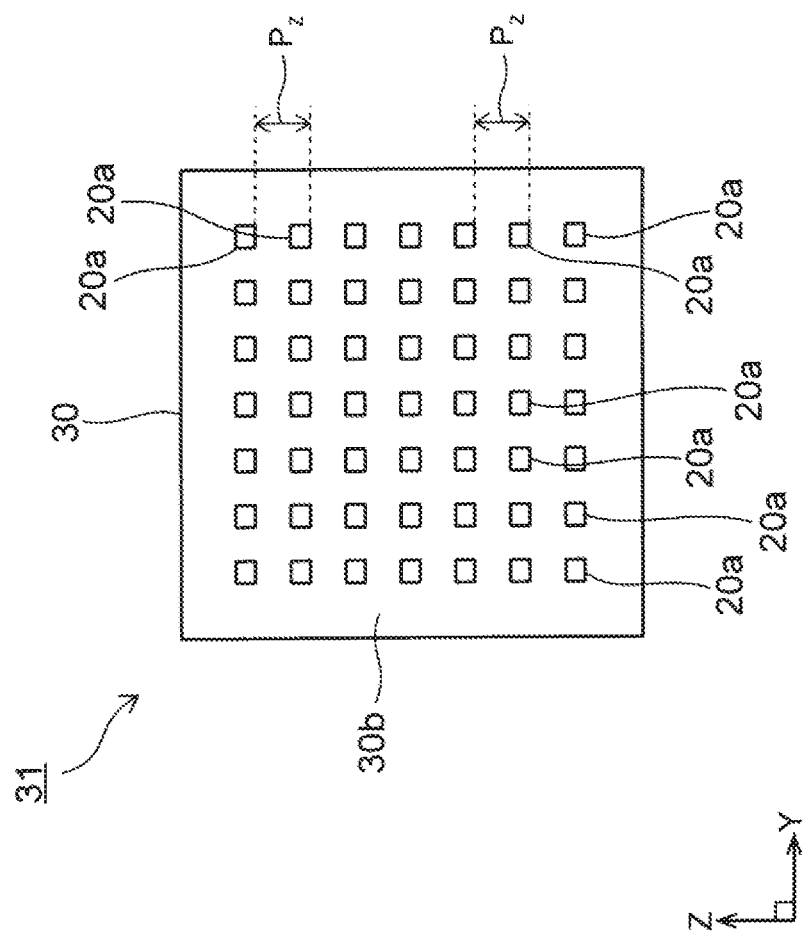
FIG. 23 is a top view of the backing member according to the first embodiment.

FIG. 23 is a top view of the backing member 31.

As described above, deformation of the leads 20a is suppressed by the insulating spacers 22a in the present embodiment. Accordingly, the Z-direction pitches $P_Z$ of the leads 20a exposed in the upper surface 30b can hardly vary from one another so that the pitches $P_Z$ can be made uniform with one another.

Next, an ultrasonic probe using the backing member 31 according to the present embodiment will be described.

Figure 24:
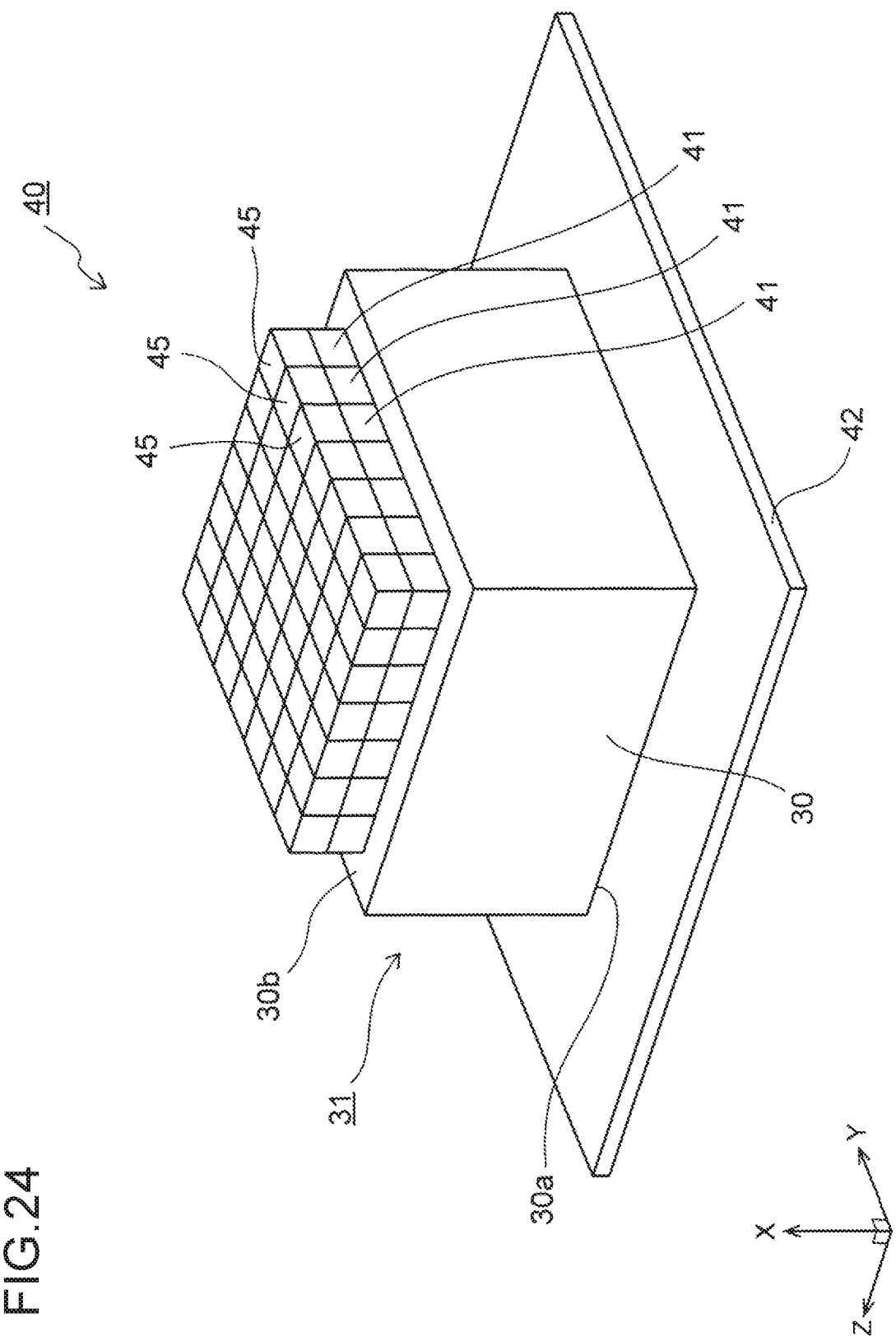
FIG. 24 is a perspective view of an ultrasonic probe according to the first embodiment.

FIG. 24 is a perspective view of the ultrasonic probe according to the present embodiment.

The ultrasonic probe 40 is provided with the backing member 31, and a plurality of piezoelectric elements 41 arranged on the upper surface 30b of the resin body 30. The piezoelectric elements 41 are elements that radiate ultrasounds onto a subject or receive echoes of the ultrasounds reflected by the subject.

An acoustic matching layer 45 made of a resin and provided for absorbing a difference of acoustic impedance between the subject and each of the piezoelectric elements 41 is provided on the piezoelectric element 41.

The ultrasonic probe 40 is used in a state in which the lower surface 30a side of the resin body 30 is fixedly bonded to a wiring substrate 42.

Ultrasounds generated by the piezoelectric elements 41 are absorbed by the resin body 30. Accordingly, unnecessary ultrasounds are not propagated to the wiring substrate 42. Further, due to the sound absorption made thus, a pulse width of each of the ultrasounds radiated on the subject is shortened so that resolution of an image can be improved.

Figure 25:
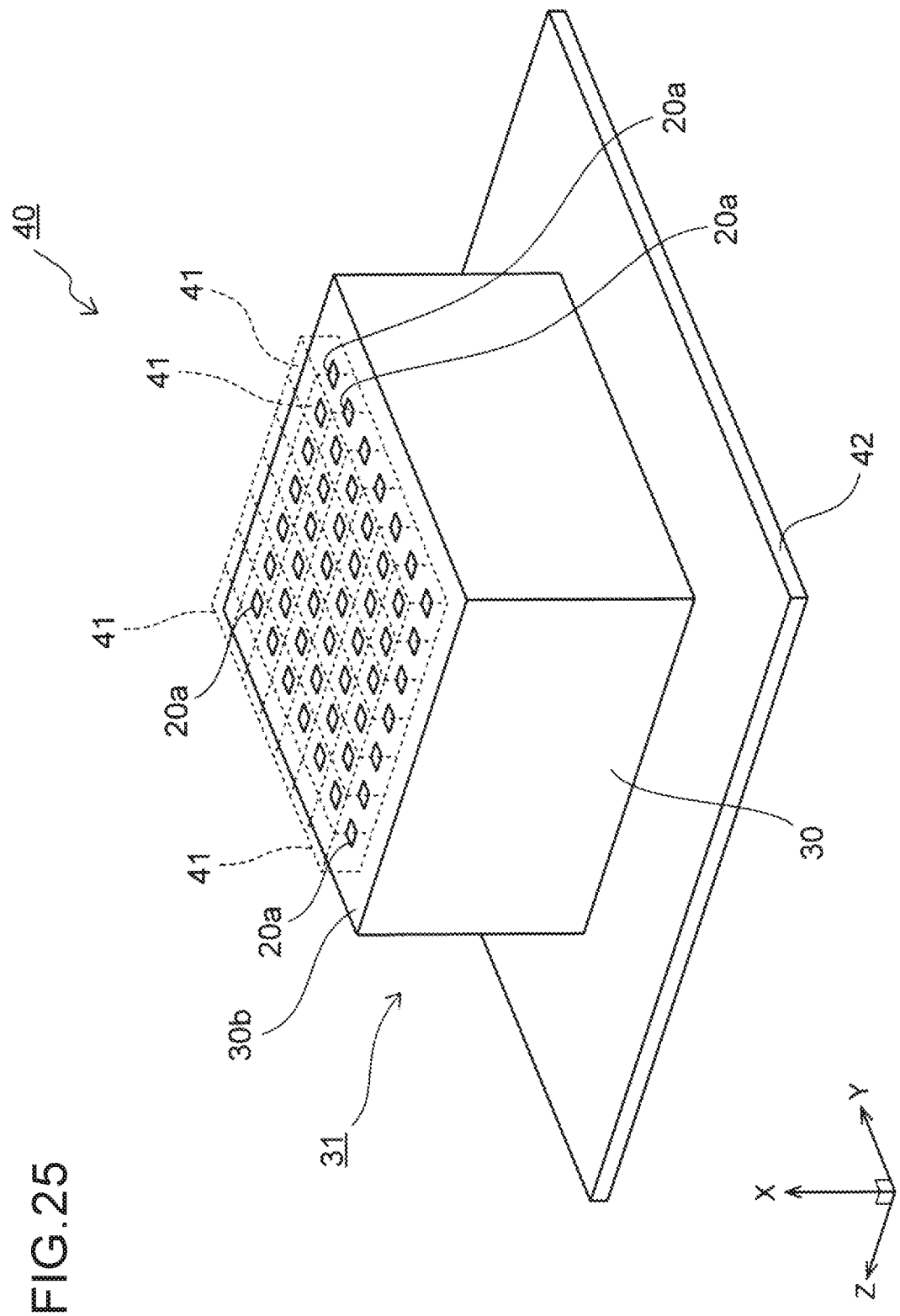
FIG. 25 is a perspective view showing a positional relation between each of the leads and each of piezoelectric elements in the first embodiment.

FIG. 25 is a perspective view showing a positional relation between each of the leads 20a and each of the piezoelectric elements 41.

As shown in FIG. 25, the piezoelectric elements 41 are provided on the leads 20a respectively and correspondingly. The leads 20a play roles of electrically connecting the piezoelectric elements 41 to the wiring substrate 42 respectively. Thus, signals are exchanged between the piezoelectric elements 41 and the wiring substrate 42.

On this occasion, the pitches $P_Z$ of the leads 20a can be suppressed from varying from one another as in FIG. 23 in the present embodiment. Accordingly, the piezoelectric elements 41 and the leads 20a can be suppressed from being displaced from each other respectively.

According to the present embodiment that has been described above, the leads 20a are supported from below by the insulating spacers 22a, and the convex portions 20b of the leads 20a are brought into contact with the insulating spacers 22a from below, as shown in FIG. 20. Thus, the leads 20a can be suppressed from being deformed upward/downward. Thus, as shown in FIG. 23, the pitches $P_Z$ of the leads 20a can be suppressed from varying from one another so that the leads 20a and the piezoelectric elements 41 can be excellently electrically connected to each other respectively. Accordingly, reliability of the ultrasonic probe 40 can be improved.

Moreover, since deformation of the leads 20a is suppressed as described above, the danger of causing electric short-circuiting between adjacent ones of the leads 20a in the Z direction is reduced. Accordingly, the reliability of the ultrasonic probe 40 can be more improved.

Next, a manufacturing method of the lead frame 20 used in the present embodiment will be described.

Figure 26A:
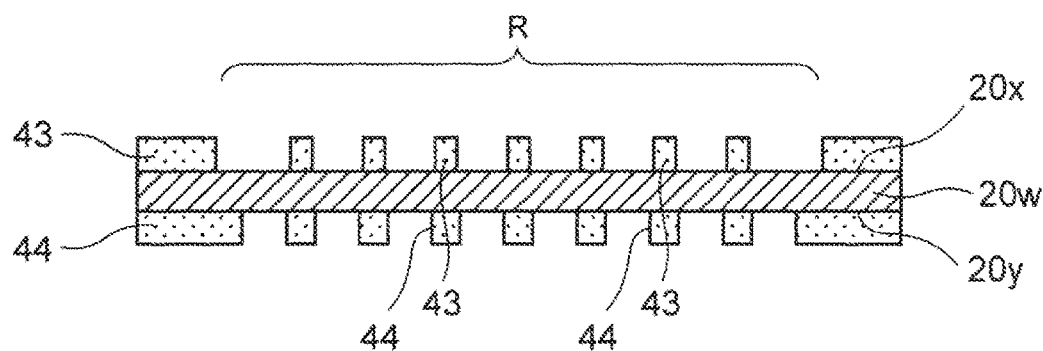
FIGS. 26A to 26C are sectional views in process of manufacturing the lead frame according to the first embodiment.
Figure 26B:
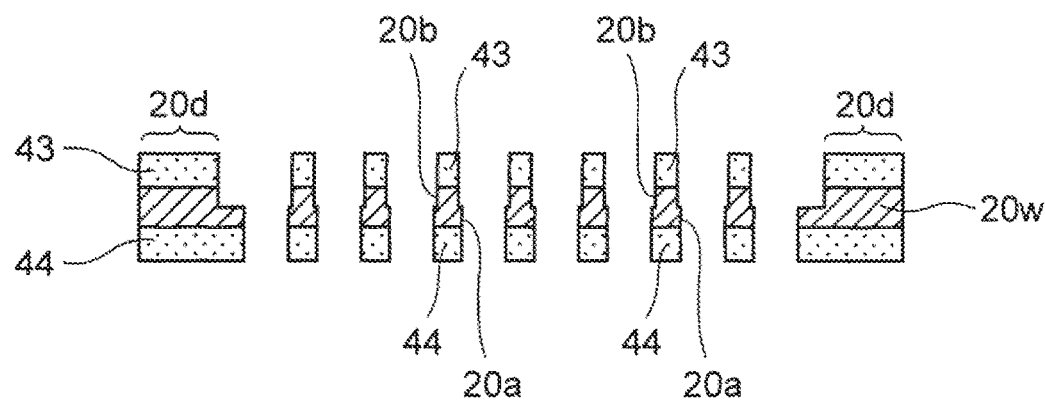
Figure 26C:
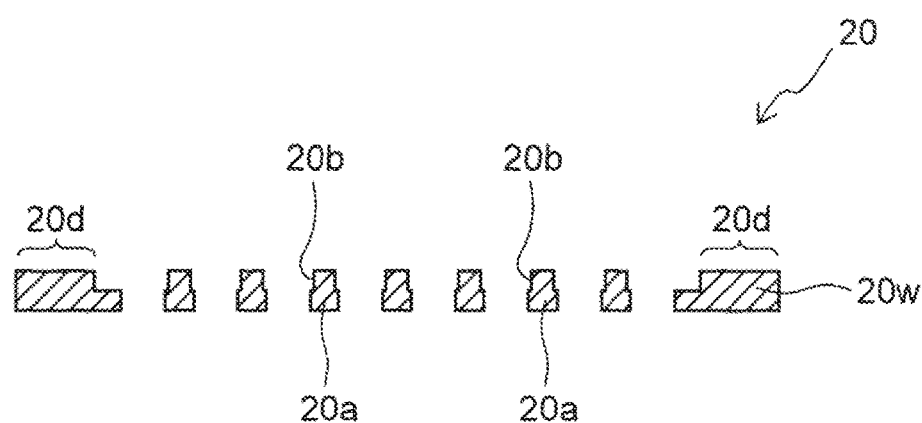

FIGS. 26A to 26C are sectional views in process of manufacturing the lead frame 20 according to the present embodiment. FIGS. 26A to 26C correspond to the sectional views taken along the line I-I of the aforementioned FIG. 11.

First, a copper plate 20w about 150 μm thick is prepared, and a first resist pattern 43 and a second resist pattern 44 are formed on a front surface 20x and a back surface 20y of the copper plate 20w respectively, as shown in FIG. 26A.

In particular, the first resist pattern 43 has island-like planar shapes corresponding to convex portions 20b (see FIG. 11) in each product region R, and covers the copper plate 20w outside the product region R.

In addition, the second resist pattern 44 has strip-like planar shapes corresponding to leads 20a (see FIG. 11) in the product region R, and covers the copper plate 20w outside the product region R.

Next, the copper plate 20w is wet-etched from its opposite surfaces with the resist patterns 43 and 44 as masks to thereby form the leads 20a and the convex portions 20b, as shown in FIG. 26B. On this occasion, a portion of the copper plate 20w covered with both the first resist pattern 43 and the second resist pattern 44 is not etched but formed into a thick portion 20d.

As shown in FIG. 26C, the resist patterns 43 and 44 are removed to thereby complete the lead frame 20 according to the present embodiment.

Second Embodiment

In the first embodiment, as shown in the dotted line circle of FIG. 20, the convex portions 20b are provided on the leads 20a, and the convex portions 20b are brought into contact with the back surfaces 22y of the insulating spacers 22a. Thus, upward deformation of the leads 20a is suppressed. On the other hand, convex portions 20b will be omitted from the present embodiment as follows.

Figure 27:
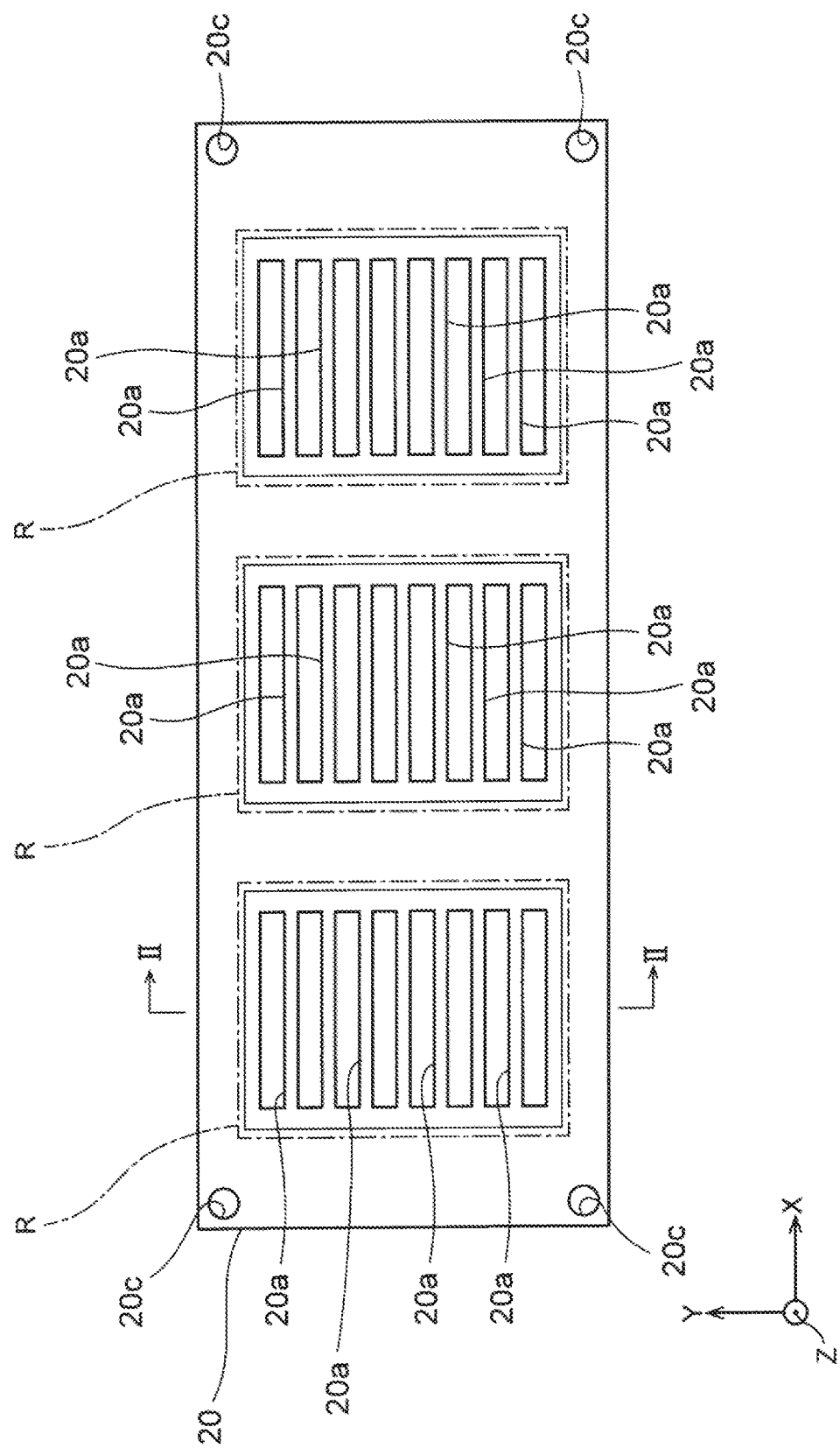
FIG. 27 is a plan view of a lead frame according to a second embodiment.

FIG. 27 is a plan view of a lead frame 20 according to the present embodiment.

Incidentally, elements the same as those described in the first embodiment will be referred to by the same signs as those in the first embodiment, and description thereof will be omitted below.

In a similar manner to or the same manner as the first embodiment, a copper plate is machined so that the lead frame 20 is manufactured. The lead frame 20 is provided with a plurality of leads 20a extending in an X direction. No convex portions 20b (see FIG. 11) are formed on the leads 20a respectively, differently from the first embodiment.

Figure 28:
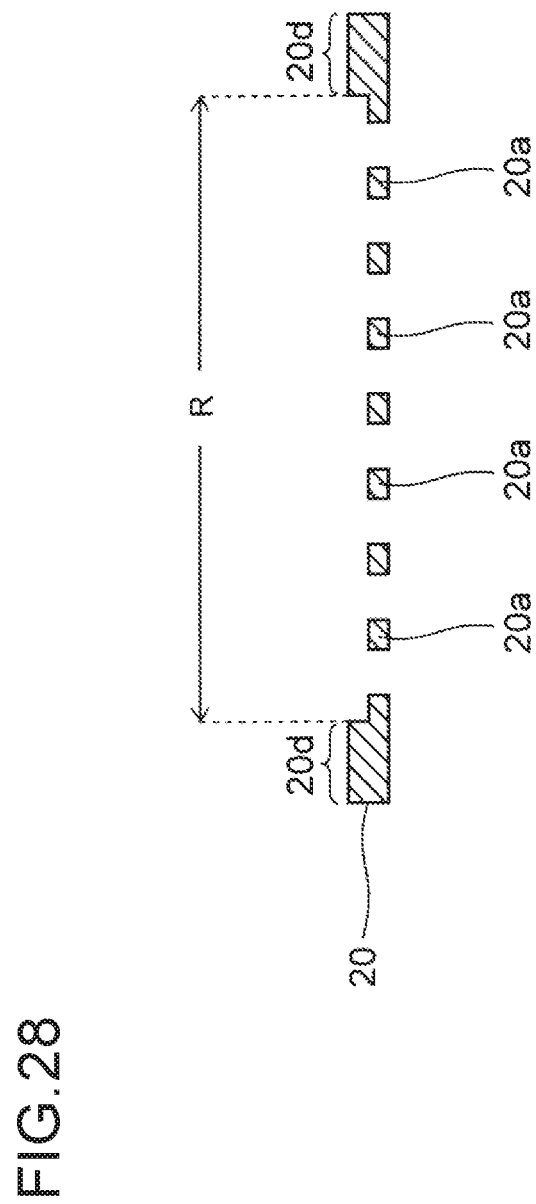
FIG. 28 is a sectional view taken along a line of FIG. 27.

FIG. 28 is a sectional view taken along a line II-II of FIG. 27.

As shown in FIG. 28, a thick portion 20d is formed in the lead frame 20 outside product regions R. Thus, rigidity of the lead frame 20 is enhanced so that handling of the lead frame 20 can be easy, as described above in the first embodiment.

Next, a manufacturing method of backing members using the lead frames 20 will be described.

Figure 29:
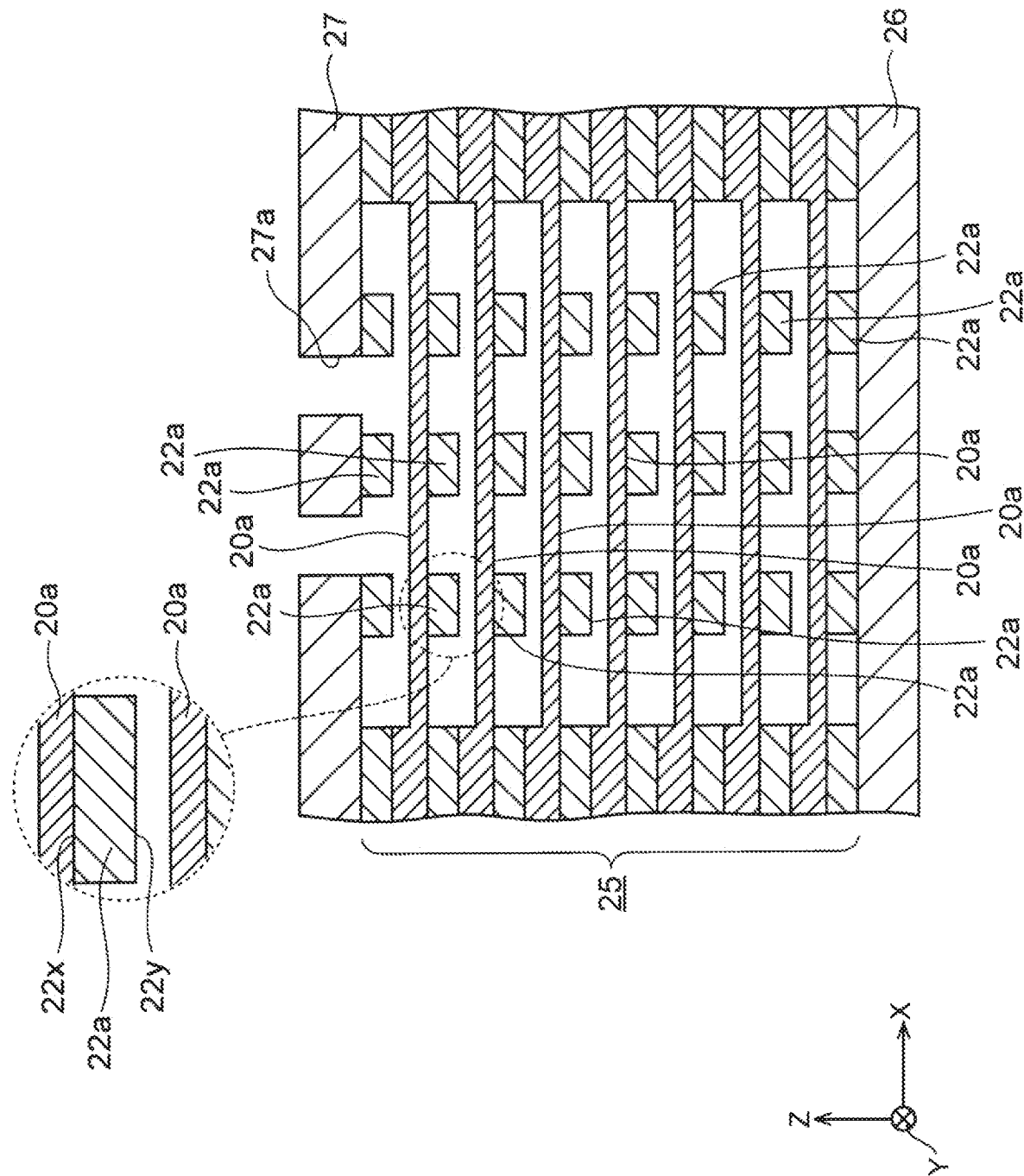
FIG. 29 is a sectional view in process of manufacturing backing members according to the second embodiment (Part 1)
Figure 30:
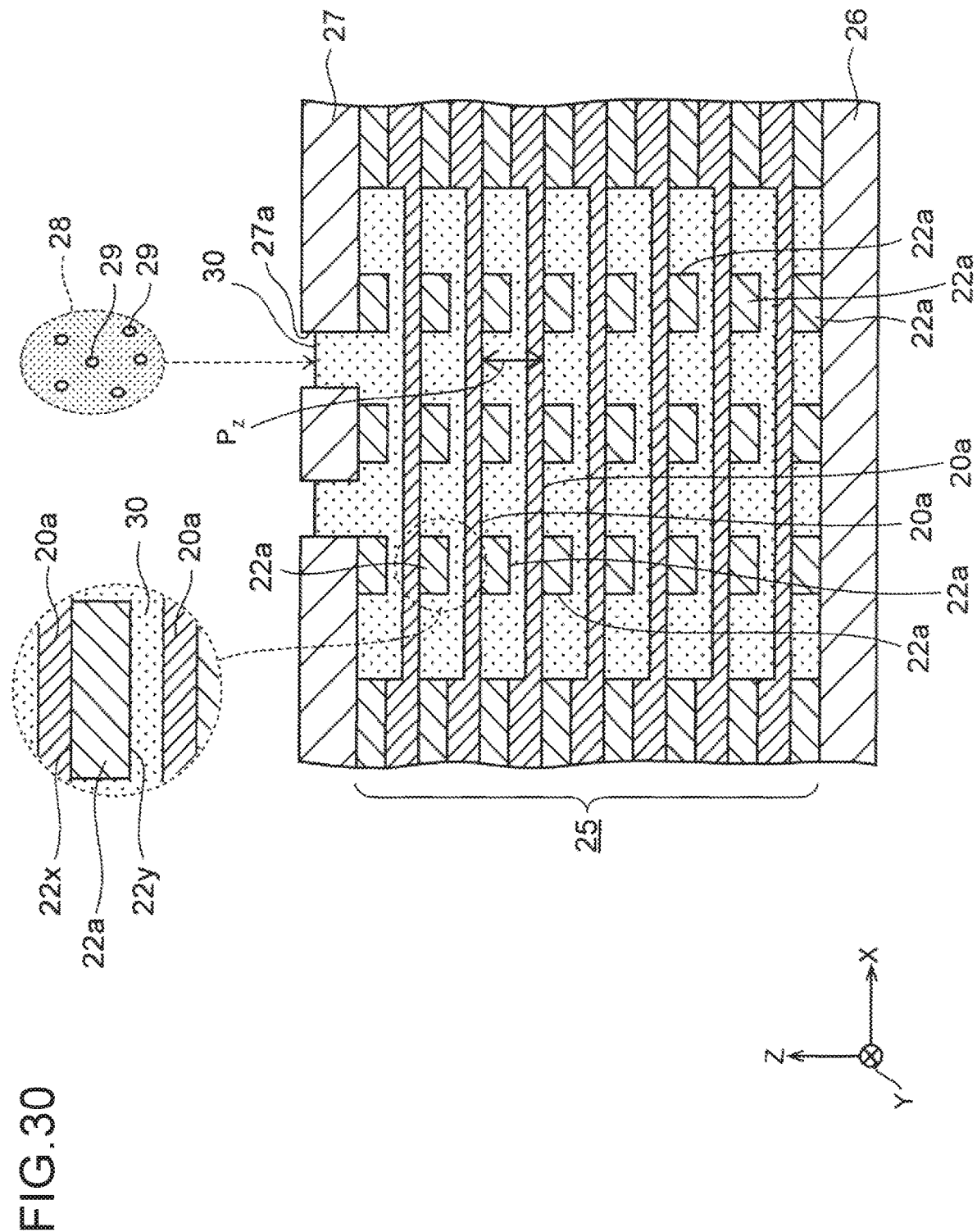
FIG. 30 is a sectional view in the process of manufacturing the backing members according to the second embodiment (Part 2)
Figure 31:
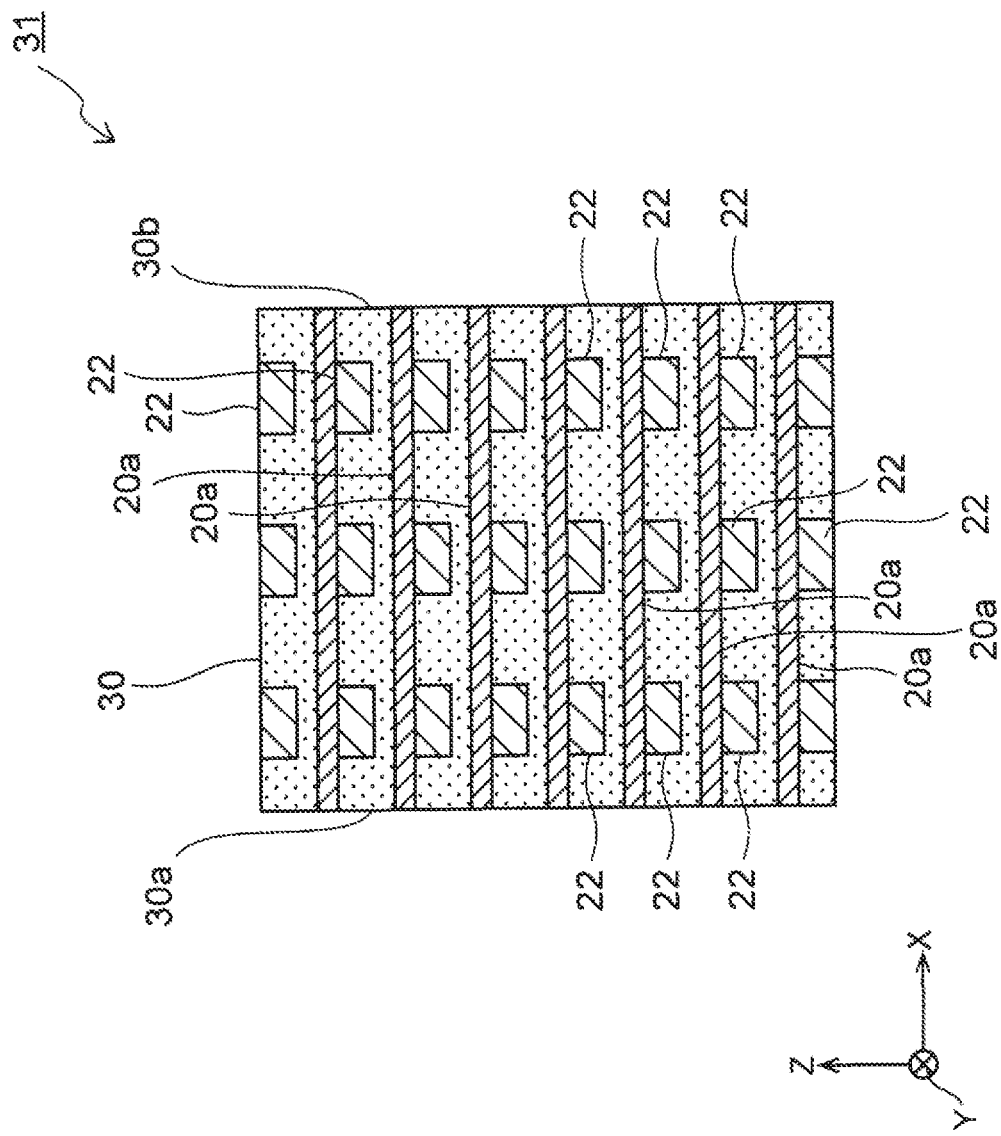
FIG. 31 is a sectional view in the process of manufacturing the backing members according to the second embodiment (Part 3)

FIGS. 29 to 31 are sectional views in process of manufacturing the backing members according to the present embodiment.

Incidentally, in FIGS. 29 to 31, elements the same as those which have been described above in the first embodiment will be referred to by the same signs as those in the first embodiment, and description thereof will be omitted below.

First, as shown in FIG. 29, a stacked body 25 including lead frames 20 and spacer members 22 stacked on one another alternately is prepared in a similar manner to or the same manner as the step of FIG. 19 in the first embodiment. The stacked body 25 is interposed between a lower support plate 26 and an upper support plate 27.

As shown in a dotted line circle of FIG. 29, front surfaces 22x of insulating spacers 22a contact leads 20a from below in this state. Accordingly, downward deformation of the leads 20a can be suppressed by the insulating spacers 22a. On the other hand, back surfaces 22y of the insulating spacers 22a are separated from the leads 20a located thereunder.

Next, as shown in FIG. 30, a thermosetting resin 28 is injected from resin injection ports 27a of the upper support plate 27, and the resin 28 is thermally cured in conditions that heating temperature is set at 150° C. and heating time is set at two hours. As a result, resin bodies 30 are formed. For example, a thermosetting epoxy resin added with fillers 29 of tungsten particles etc. may be used as the resin 28.

On this occasion, downward deformation of the leads 20a is suppressed by the insulating spacers 22a. Accordingly, the leads 20a can be hardly deformed downward by pressure when the resin 28 is supplied or by force when the resin 28 is thermally cured and contracted, so that pitches $P_Z$ of the leads 20a can be suppressed from varying from one another.

Next, after the stacked body 25 is extracted from a space between the lower support plate 26 and the upper support plate 27 in a similar manner to or the same manner as the step of FIG. 21, the stacked body 25 is cut to be divided into individual pieces of backing members 31, as shown in FIG. 31.

FIG. 32 is a perspective view showing a positional relation between each of the leads 20a and each of piezoelectric elements 41 in an ultrasonic probe 40 provided with the backing member 31.

As shown in FIG. 32, the leads 20a are exposed in an upper surface 30b of the resin body 30, and the leads 20a are electrically connected to the piezoelectric elements 41 respectively. On this occasion, in the present embodiment, the pitches $P_Z$ (see FIG. 30) of the leads 20a are suppressed from varying from one another, as described above. Accordingly, the piezoelectric elements 41 and the leads 20a can be suppressed from being displaced from each other respectively.

According to the present embodiment which has been described above, the front surfaces 22x of the insulating spacers 22a are brought into contact with the leads 20a from below, as shown in FIG. 30. Accordingly, the pitches $P_Z$ of the leads 20a can hardly vary from one another. As a result, the leads 20a and the piezoelectric elements 41 can be suppressed from being displaced from each other respectively so that the leads 20a and the piezoelectric elements 41 can be excellently electrically connected to each other respectively. Accordingly, the reliability of the ultrasonic probe 40 can be improved.

Various aspects of the subject matter described herein are set out non-exhaustively in the following numbered clauses:

1) A manufacturing method of a backing member, the method comprising:
preparing a plurality of lead frames each of which comprises a plurality of leads which extend in a first direction and disposed at pitches;
preparing a plurality of spacer members each of which comprises a plurality of insulating spacers which extend in a second direction intersecting with the first direction;
stacking the lead frames and the spacer members on one another alternately to thereby prepare a stacked body including the lead frames and the spacer members;
filling a space between adjacent ones of the leads with a resin to thereby form a resin body in which the leads are embedded; and
cutting the resin body to thereby expose the leads in each of a lower surface and an upper surface of the resin body, wherein the lower surface and the upper surface is opposite to each other.

2) The manufacturing method according to clause (1), wherein in preparing the lead frames, a convex portion is formed on each of the leads to protrude outward in a third direction intersecting with the first direction and the second direction.

3) The manufacturing method according to clause (1), wherein:
preparing the lead frames comprises:
forming the leads on a metal plate; and
making a thickness of the metal plate in a first region including the leads thinner than a thickness of the metal plate in a region outside the first region in plan view.

As described above, the exemplary embodiment and the modification are described in detail. However, the present invention is not limited to the above-described embodiment and the modification, and various modifications and replacements are applied to the above-described embodiment and the modifications without departing from the scope of claims.

What is claimed is:

1. A backing member comprising:
a resin body comprising a lower surface and an upper surface opposite to each other, wherein a first direction of the resin body extends from the lower surface toward the upper surface, a second direction of the resin body is orthogonal to the first direction, and a third direction of the resin body is orthogonal to the first direction and the second direction;
a plurality of leads each of which extends in the first direction from the lower surface toward the upper surface, and that are embedded in the resin body at a first pitch in the second direction and at a second pitch in the third direction; and
a plurality of insulating spacers embedded in the resin body, each of the plurality of insulating spacers is provided between a respective adjacent pair of leads among the plurality of leads in the third direction, the plurality of insulating spacers each extends in the second direction, the plurality of insulating spacers respectively contact the plurality of leads, and the plurality of insulating spacers are embedded in the resin body at a third pitch in the first direction and at a fourth pitch in the third direction,
wherein
each of the plurality of insulating spacers comprises a front surface that directly contacts corresponding ones of the plurality of leads, and a back surface that is opposite to the front surface in the third direction, and
each of the plurality of leads comprises a convex portion that protrudes outward in the third direction to contact the back surface of a corresponding one of the plurality of insulating spacers.

2. The backing member according to claim 1, wherein each convex portion is shaped like a circle when seen from the third direction.

3. The backing member according to claim 1, wherein the plurality of insulating spacers are formed of a resin.

4. An ultrasonic probe comprising:
a resin body comprising a lower surface and an upper surface opposite to each other, wherein a first direction of the resin body extends from the lower surface toward the upper surface, a second direction of the resin body is orthogonal to the first direction, and a third direction of the resin body is orthogonal to the first direction and the second direction;
a plurality of leads each of which extends in the first direction from the lower surface toward the upper surface, and that are embedded in the resin body at a first pitch in the second direction and at a second pitch in the third direction;

a plurality of insulating spacers embedded in the resin body, each of the plurality of insulating spacers is provided between a respective adjacent pair of leads among the plurality of leads in the third direction, the plurality of insulating spacers each extends in second direction, the plurality of insulating spacers respectively contact the plurality of leads, and the plurality of insulating spacers are embedded in the resin body at a third pitch in the first direction and at a fourth pitch in the third direction; and a plurality of piezoelectric elements each of which is arranged on the upper surface and connected to a corresponding one of the plurality of leads exposed in the upper surface, wherein each of the plurality of insulating spacers comprises a front surface that directly contacts corresponding ones of the plurality of leads, and a back surface that is opposite to the front surface in the third direction, and each of the plurality of leads comprises a convex portion that protrudes outward in the third direction to contact the back surface of a corresponding one of the plurality of insulating spacers.

5. The backing member according to claim 1, wherein:
the front surface of each of the plurality of insulating spacers is a flat, planar surface.

6. The ultrasonic probe according to claim 4, wherein:
the front surface of each of the plurality of insulating spacers is a flat, planar surface.

7. The backing member according to claim 1, wherein:
at least two insulating spacers of the plurality of insulating spacers are embedded in the resin body at a same position in the third direction and at the third pitch in the first direction, and at least two insulating spacers of the plurality of insulating spacers are embedded in the resin body at a same position in the first direction and at the fourth pitch in the third direction.

8. The ultrasonic probe according to claim 4, wherein:
at least two insulating spacers of the plurality of insulating spacers are embedded in the resin body at a same position in the third direction and at the third pitch in the first direction, and at least two insulating spacers of the plurality of insulating spacers are embedded in the resin body at a same position in the first direction and at the fourth pitch in the third direction.

* * * * *